(12) United States Patent
Hibner et al.

(10) Patent No.: US 8,162,848 B2
(45) Date of Patent: Apr. 24, 2012

(54) MRI BIOPSY TARGETING CUBE WITH ECCENTRIC LOCK

(75) Inventors: John A. Hibner, Mason, OH (US); Anil R. Jadhav, Maharashtra (IN); Nitin P. Wale, Maharashtra (IN); Santosh G. Deshmukh, Maharashtra (IN); Ajay D. Pawar, Maharashtra (IN); Abhijit G. Kulkarni, Maharashtra (IN)

(73) Assignee: Devicor Medical Products, Inc., Cincinnati, OH (US)

( * ) Notice: Subject to any disclaimer, the term of this patent is extended or adjusted under 35 U.S.C. 154(b) by 448 days.

(21) Appl. No.: 12/580,292

(22) Filed: Oct. 16, 2009

(65) Prior Publication Data

US 2011/0092848 A1    Apr. 21, 2011

(51) Int. Cl.
*A61B 10/00*    (2006.01)
*A61B 19/00*    (2006.01)

(52) U.S. Cl. ......... 600/562; 600/564; 600/567; 606/130

(58) Field of Classification Search .......... 600/562–572; 606/130

See application file for complete search history.

(56) References Cited

U.S. PATENT DOCUMENTS

| | | | |
|---|---|---|---|
| 5,526,822 A | 6/1996 | Burbank et al. | |
| 5,649,547 A | 7/1997 | Ritchart et al. | |
| 5,769,086 A | 6/1998 | Ritchart et al. | |
| 5,775,333 A | 7/1998 | Burbank et al. | |
| 5,928,164 A | 7/1999 | Burbank et al. | |
| 5,964,716 A | 10/1999 | Gregoire et al. | |
| 5,980,469 A | 11/1999 | Burbank et al. | |
| 6,007,497 A | 12/1999 | Huitema | |
| 6,017,316 A | 1/2000 | Ritchart et al. | |
| 6,077,230 A | 6/2000 | Gregoire et al. | |
| 6,086,544 A | 7/2000 | Hibner et al. | |
| 6,120,462 A | 9/2000 | Hibner et al. | |
| 6,228,055 B1 | 5/2001 | Foerster et al. | |
| 6,231,522 B1 | 5/2001 | Voegele et al. | |
| 6,273,862 B1 | 8/2001 | Privitera et al. | |
| 6,626,849 B2 | 9/2003 | Huitema et al. | |
| 6,752,768 B2 | 6/2004 | Burdorff et al. | |
| 7,442,171 B2 | 10/2008 | Stephenson et al. | |
| 7,740,593 B2 * | 6/2010 | Shabaz | 600/562 |
| 7,744,543 B2 * | 6/2010 | Shabaz | 600/562 |
| 2003/0199753 A1 | 10/2003 | Hibner et al. | |
| 2005/0283069 A1 | 12/2005 | Hughes et al. | |
| 2007/0135821 A1 * | 6/2007 | Shabaz | 606/130 |
| 2007/0255168 A1 | 11/2007 | Hibner et al. | |

(Continued)

OTHER PUBLICATIONS

U.S. Appl. No. 12/337,814, filed Dec. 18, 2008, Parihar et al.

(Continued)

*Primary Examiner* — Jeffrey G Hoekstra
(74) *Attorney, Agent, or Firm* — Frost Brown Todd LLC

(57) ABSTRACT

A biopsy system comprises a control module, a localization assembly, a biopsy device, and a targeting cube. A probe and/or other associated components of the biopsy device are configured to selectively couple with the targeting cube, which is configured to selectively couple with a grid plate. The targeting cube may comprise an eccentric lock for securing the targeting cube within the grid plate. The targeting cube may further comprise an elastomeric insert positioned within guide holes of the targeting cube for securing the probe and/or other associated components within the guide hole of the targeting cube. The guide holes of the targeting cube may alternatively, or in addition, include an elastomeric retaining ring within the passageway of the guide hole.

20 Claims, 30 Drawing Sheets

U.S. PATENT DOCUMENTS

| | | | |
|---|---|---|---|
| 2007/0255170 A1* | 11/2007 | Hibner et al. | 600/564 |
| 2008/0132912 A1* | 6/2008 | Shabaz | 606/130 |
| 2008/0146962 A1 | 6/2008 | Ritchie et al. | |
| 2008/0214955 A1 | 9/2008 | Speeg et al. | |
| 2008/0221480 A1 | 9/2008 | Hibner et al. | |
| 2008/0228103 A1 | 9/2008 | Ritchie et al. | |

OTHER PUBLICATIONS

U.S. Appl. No. 12/337,674, filed Dec. 18, 2008, Parihar et al.

U.S. Appl. No. 12/337,874, filed Dec. 18, 2008, Parihar et al.

U.S. Appl. No. 12/337,911, filed Dec. 18, 2008, Parihar et al.

U.S. Appl. No. 12/337,942, filed Dec. 18, 2008, Parihar et al.

U.S. Appl. No. 12/485,119, filed Jun. 16, 2009, Leimbach et al.

U.S. Appl. No. 12/485,138, filed Jun. 16, 2009, Leimbach et al.

U.S. Appl. No. 12/485,168, filed Jun. 16, 2009, Leimbach et al.

U.S. Appl. No. 12/485,278, filed Jun. 16, 2009, Leimbach et al.

U.S. Appl. No. 12/485,318, filed Jun. 16, 2009, Leimbach.

* cited by examiner

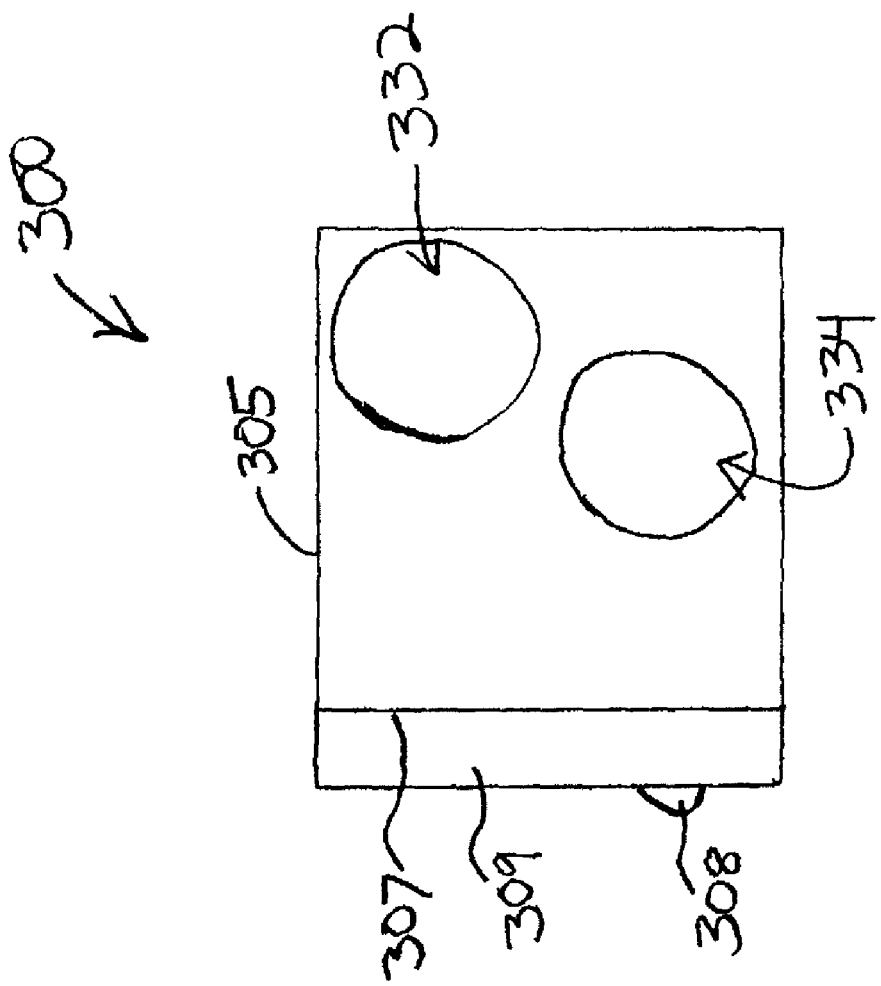

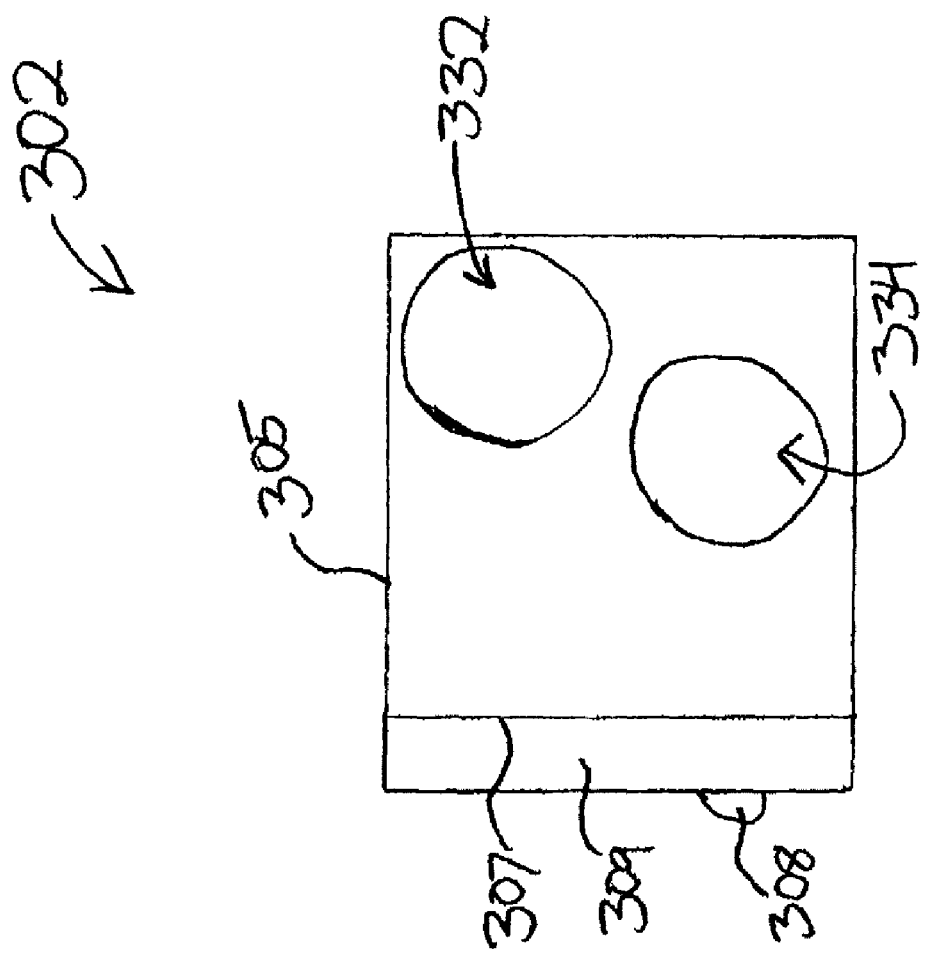

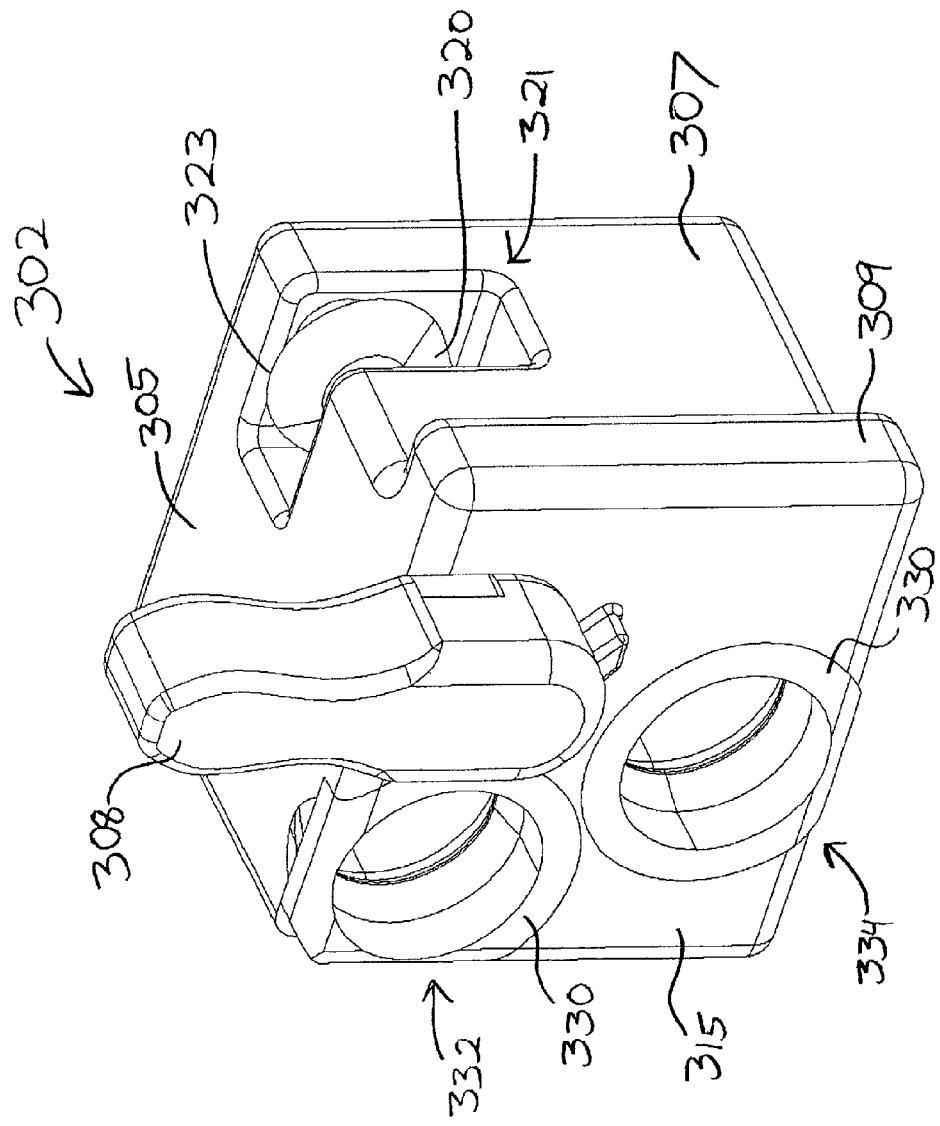

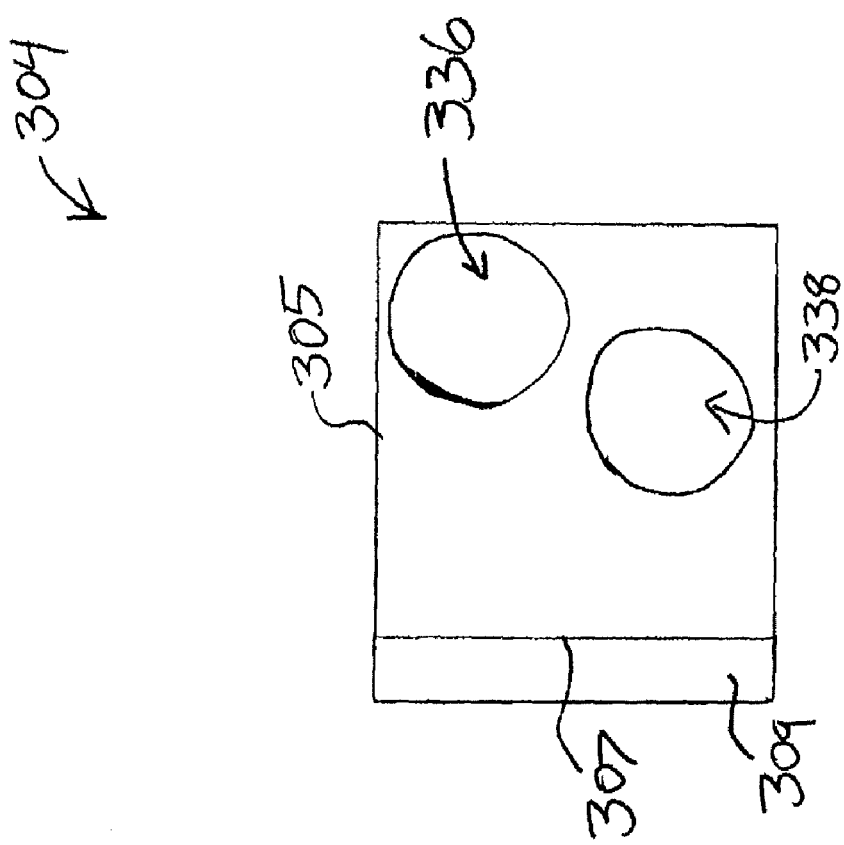

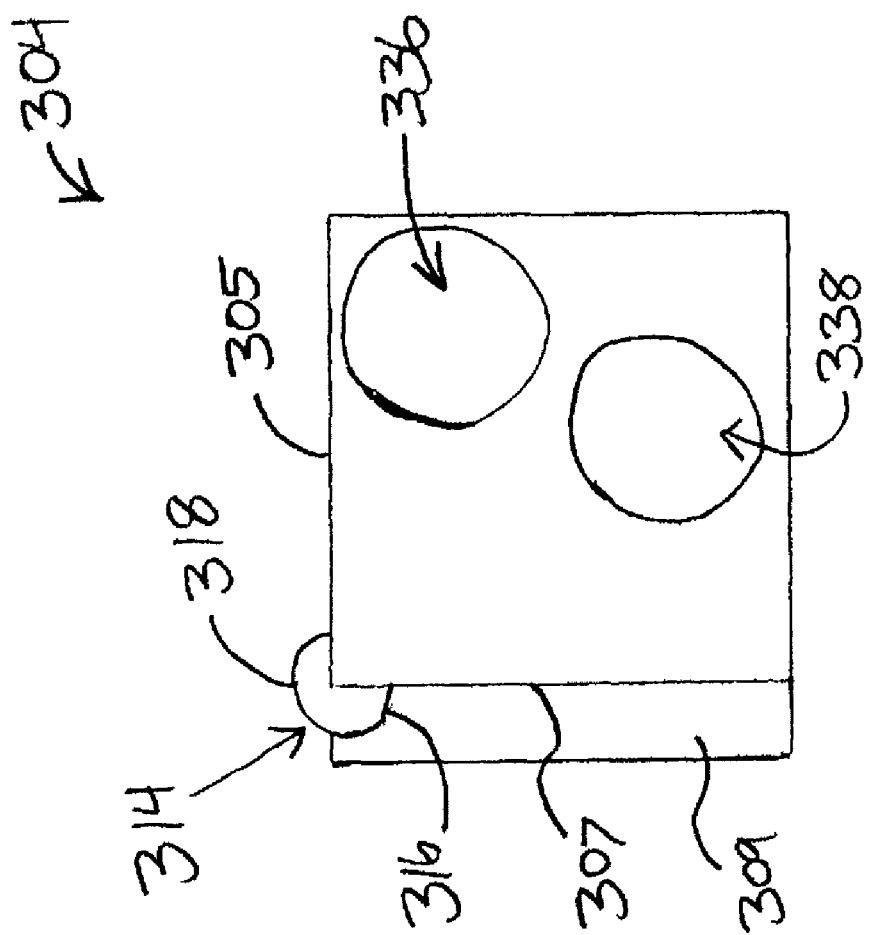

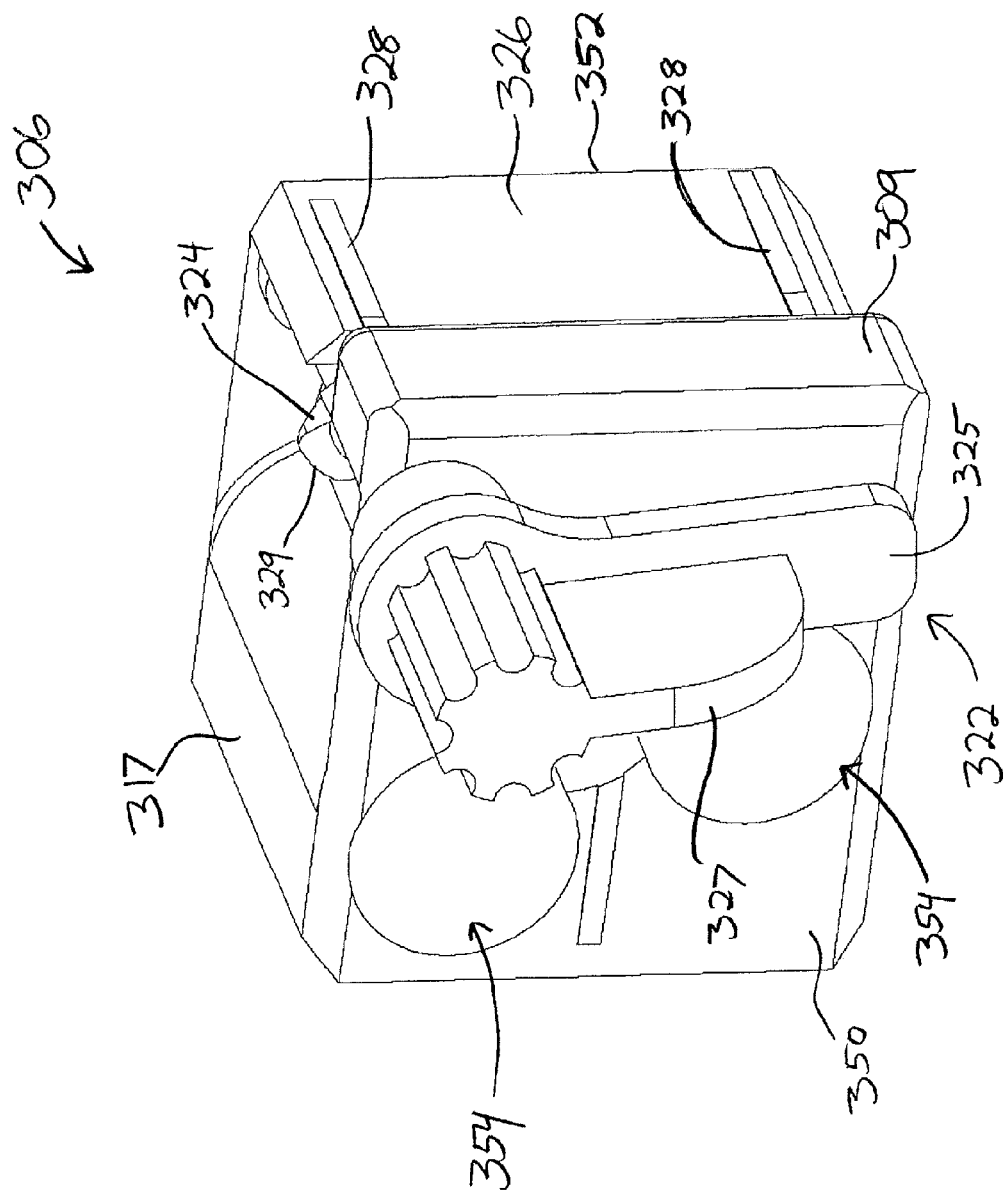

MRI BIOPSY TARGETING CUBE WITH ECCENTRIC LOCK

BACKGROUND

Biopsy samples have been obtained in a variety of ways in various medical procedures using a variety of devices. Biopsy devices may be used under stereotactic guidance, ultrasound guidance, MRI guidance, PEM guidance, BSGI guidance, or otherwise. Merely exemplary biopsy devices are disclosed in U.S. Pat. No. 6,273,862, entitled "Surgical Device for the Collection of Soft Tissue," issued Aug. 14, 2001; U.S. Pat. No. 6,231,522, entitled "Biopsy Instrument with Breakable Sample Segments," issued May 15, 2001; U.S. Pat. No. 6,228, 055, entitled "Devices for Marking and Defining Particular Locations in Body Tissue," issued May 8, 2001; U.S. Pat. No. 6,120,462, entitled "Control Method for an Automated Surgical Biopsy Device," issued Sep. 19, 2000; U.S. Pat. No. 6,086,544, entitled "Control Apparatus for an Automated Surgical Biopsy Device," issued Jul. 11, 2000; U.S. Pat. No. 6,077,230, entitled "Biopsy Instrument with Removable Extractor," issued Jun. 20, 2000; U.S. Pat. No. 6,017,316, entitled "Vacuum Control System and Method for Automated Biopsy Device," issued Jan. 25, 2000; U.S. Pat. No. 6,007, 497, entitled "Surgical Biopsy Device," issued Dec. 28, 1999; U.S. Pat. No. 5,980,469, entitled "Method and Apparatus for Automated Biopsy and Collection of Soft Tissue," issued Nov. 9, 1999; U.S. Pat. No. 5,964,716, entitled "Method of Use for a Multi-Port Biopsy Instrument," issued Oct. 12, 1999; U.S. Pat. No. 5,928,164, entitled "Apparatus for Automated Biopsy and Collection of Soft Tissue," issued Jul. 27, 1999; U.S. Pat. No. 5,775,333, entitled "Apparatus for Automated Biopsy and Collection of Soft Tissue," issued Jul. 7, 1998; U.S. Pat. No. 5,769,086, entitled "Control System and Method for Automated Biopsy Device," issued Jun. 23, 1998; U.S. Pat. No. 5,649,547, entitled "Methods and Devices for Automated Biopsy and Collection of Soft Tissue," issued Jul. 22, 1997; U.S. Pat. No. 5,526,822, entitled "Method and Apparatus for Automated Biopsy and Collection of Soft Tissue," issued Jun. 18, 1996; U.S. Pub. No. 2008/0214955, entitled "Presentation of Biopsy Sample by Biopsy Device," published Sep. 4, 2008; U.S. Pub. No. 2007/0255168, entitled "Grid and Rotatable Cube Guide Localization Fixture for Biopsy Device," published Nov. 1, 2007; U.S. Pub. No. 2007/ 0118048, entitled "Remote Thumbwheel for a Surgical Biopsy Device," published May 24, 2007; U.S. Pub. No. 2005/0283069, entitled "MRI Biopsy Device Localization Fixture," published Dec. 22, 2005; U.S. Pub. No. 2003/ 0199753, entitled "MRI Compatible Biopsy Device with Detachable Probe," published Oct. 23, 2003; U.S. Pub. No. 2003/0109803, entitled "MRI Compatible Surgical Biopsy Device," published Jun. 12, 2003; U.S. Pub. No. 2008/ 0221480, entitled "Biopsy Sample Storage," published Sep. 11, 2008; and U.S. Pub. No. 2008/0146962, entitled "Biopsy System with Vacuum Control Module," published Jun. 19, 2008. The disclosure of each of the above-cited U.S. patents and U.S. patent application Publications is incorporated by reference herein.

Some biopsy systems may provide an apparatus to guide a probe and/or other components of a biopsy device to a desired biopsy site. In some such biopsy systems, a guide cube and positioning grid plate may be used. The guide cube may be selectively located within an opening in the grid plate. The guide cube may include guide holes to receive a portion of the probe and/or other components, for example a needle, cannula, obturator, or combinations of these or other components. With the guide cube inserted in the grid plate, the probe or other components can be guided through a selected guide hole of the guide cube to arrive at a desired biopsy site. The desired biopsy site may or may not have been identified and/or targeted by one or more of the guidance approaches mentioned above. In some situations, it might be desirable to provide a guide cube with features that improve a guide cube's use with one or more positioning grid plates. Merely exemplary biopsy device guides are disclosed in U.S. patent application Ser. No. 12/485,119, entitled "Biopsy Targeting Cube with Elastomeric Edges," filed Jun. 16, 2009; U.S. patent application Ser. No. 12/485,138, entitled "Biopsy Targeting Cube with Elastomeric Body," filed Jun. 16, 2009; U.S. patent application Ser. No. 12/485,168, entitled "Biopsy Targeting Cube with Malleable Members," filed Jun. 16, 2009; U.S. patent application Ser. No. 12/485,278, entitled "Biopsy Targeting Cube with Angled Interface," filed Jun. 16, 2009; and U.S. patent application Ser. No. 12/485,318, entitled "Biopsy Targeting Cube with Living Hinges," filed Jun. 16, 2009. The disclosure of each of the above-cited U.S. patent applications is incorporated by reference herein.

While several systems and methods have been made and used for obtaining a biopsy sample, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings. In the drawings, like numerals represent like elements throughout the several views.

FIG. 16B is a rear elevational view of the guide cube of 16A, with the lock in the unlocked position.

FIG. 17B is a rear elevational view of the guide cube of FIG. 17A, with the lock in the unlocked position.

FIG. 17C is a front perspective view of the guide cube of FIG. 17A, with the lock in a locked position.

FIG. 18B is a rear elevational view of the guide cube of FIG. 18A, with the lock in the unlocked position.

FIG. 18D is a rear elevational view of the guide cube of FIG. 18C, with the lock in the locked position.

FIG. 19A is a front perspective view of another guide cube having a lever actuated eccentric ceramic lock, with the lock in an unlocked position.

Figure 1:
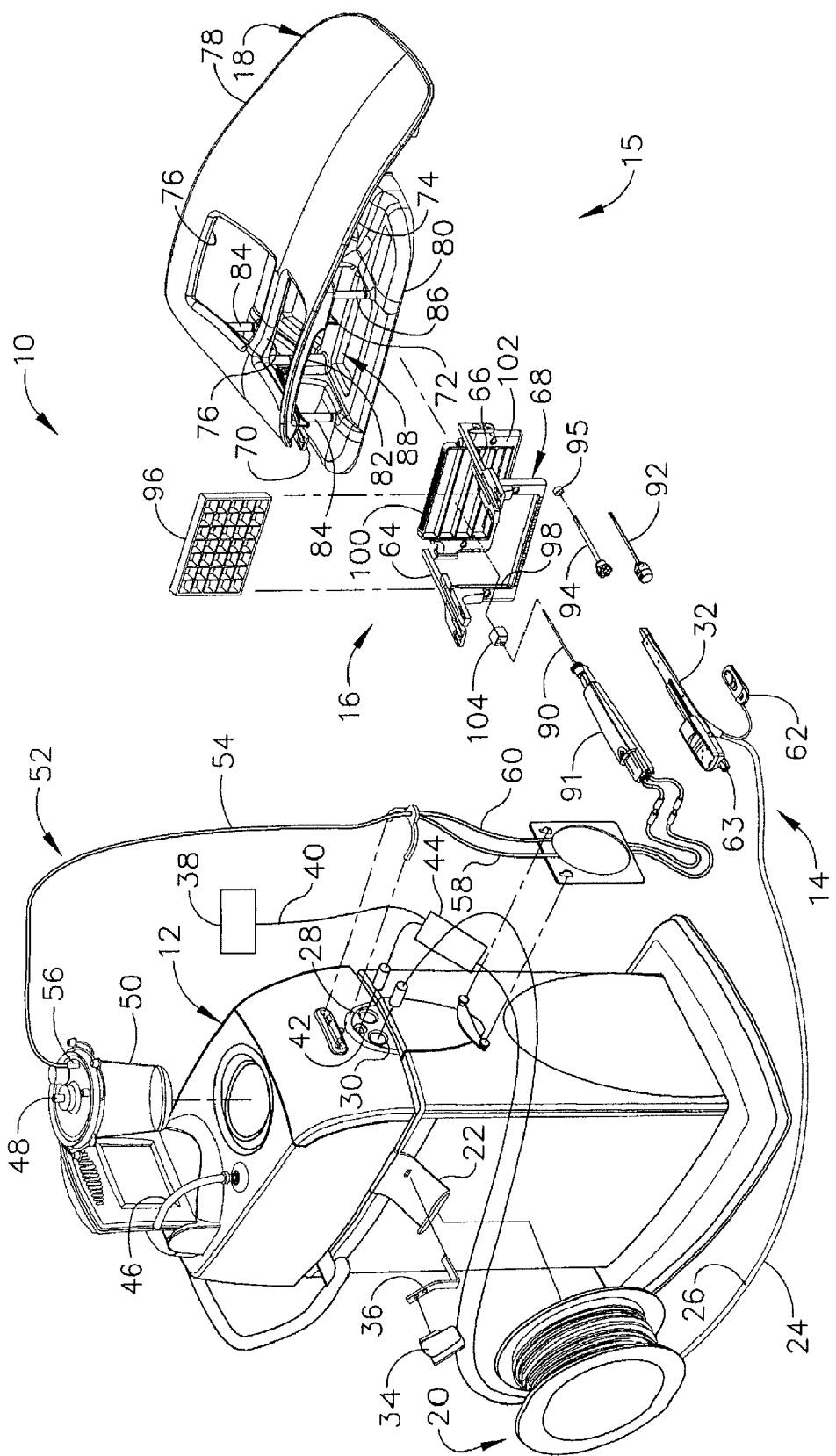
FIG. 1 is a perspective view of a biopsy system including a control module remotely coupled to a biopsy device, and including a localization assembly.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples should not be used to limit the scope of the present invention. Other features, aspects, and advantages of the versions disclosed herein will become apparent to those skilled in the art from the following description, which is by way of illustration, one of the best modes contemplated for carrying out the invention. As will be realized, the versions described herein are capable of other different and obvious aspects, all without departing from the invention. Accordingly, the drawings and descriptions should be regarded as illustrative in nature and not restrictive.

As shown in the figures, an exemplary magnetic resonance imaging (MRI or MR imaging) compatible biopsy system may include a control module (12), localization assembly (15), and biopsy device (14). In particular, localization assembly (15) is configured to localize a patient's breast and guide needle (90) of biopsy device (14) to a targeted area within the patient's breast; while control module (12) is operable to control biopsy device (14) after needle (90) has been introduced to the target site. These components and their sub-components will be discussed further below. In addition, guide cubes for use with various localization assemblies will be discussed. While this disclosure may reference the biopsy system as compatible with MRI and MRI equipment and devices, it should be appreciated that other imaging techniques and equipment and devices may be used with the components described below, including but not limited to stereotactic, ultrasound, PEM, BSGI, and/or other imaging techniques and equipment.

I. Control Module

Figure 2:
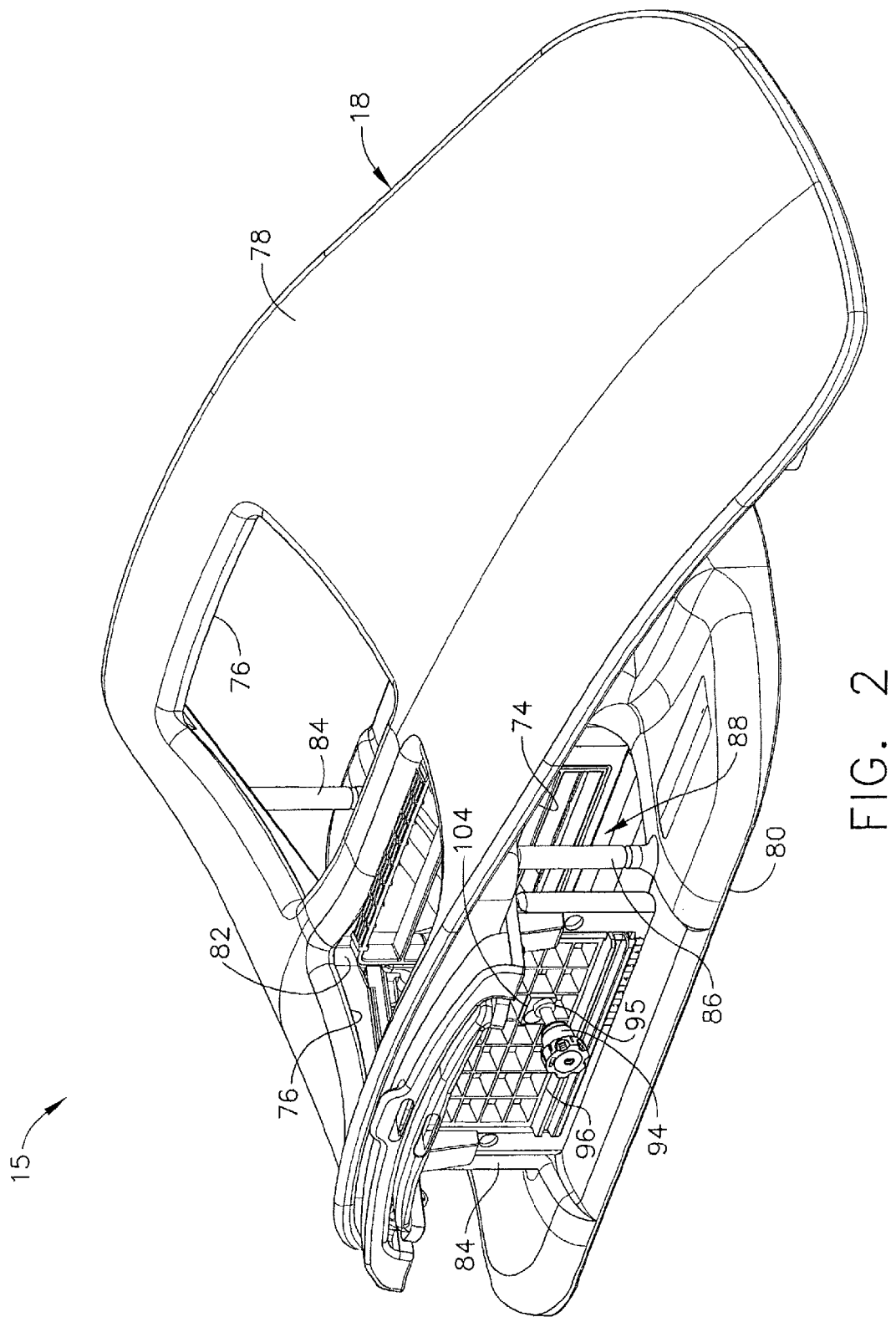
FIG. 2 is a perspective view of a breast coil of the localization assembly of FIG. 1.
Figure 3:
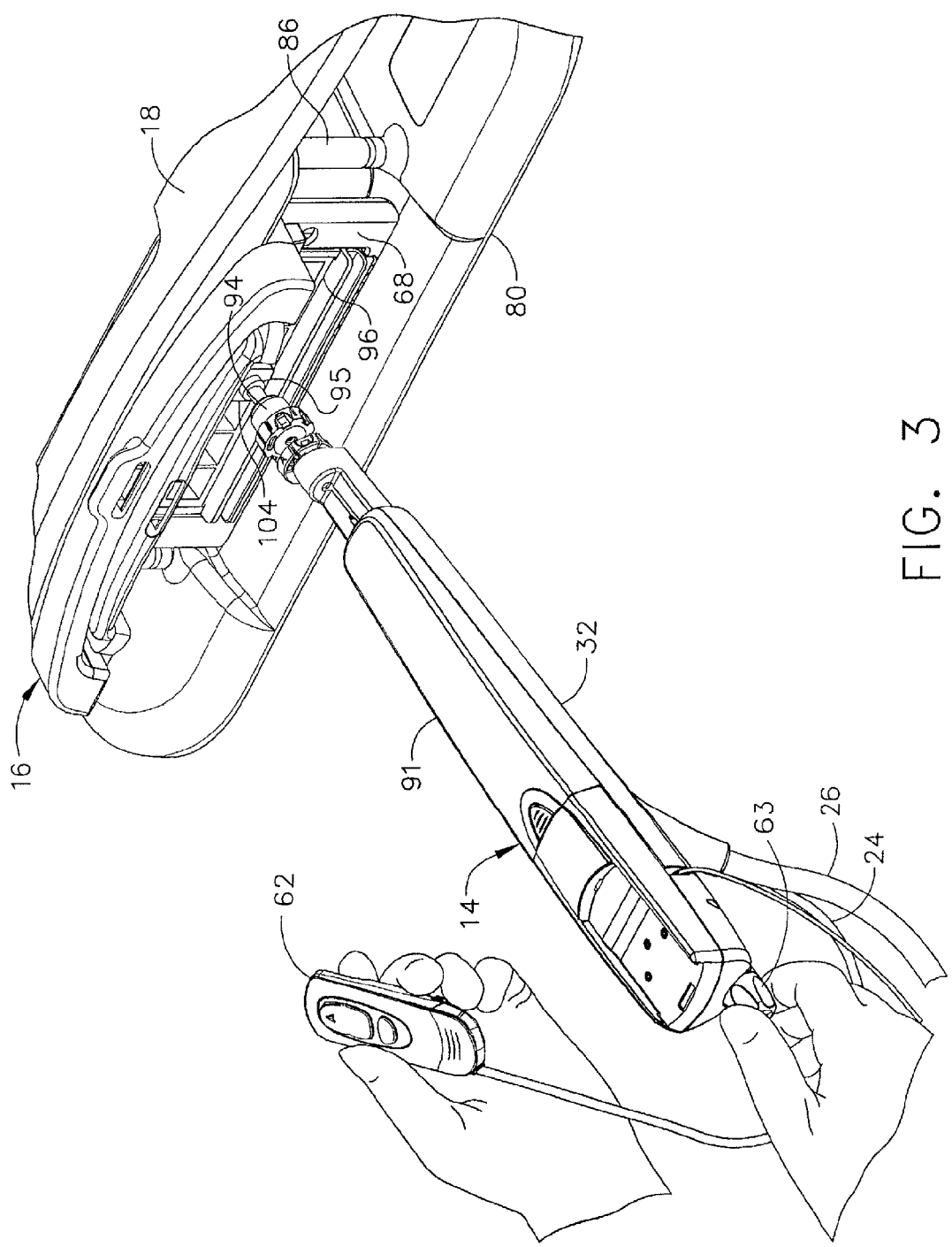
FIG. 3 is a perspective view of the biopsy device inserted through the guide cube of the localization assembly of FIG. 1.

In FIGS. 1-3, MRI compatible biopsy system (10) has control module (12) that may be placed outside of a shielded room containing an MRI machine (not shown) or at least spaced away to mitigate detrimental interaction with its strong magnetic field and/or sensitive radio frequency (RF) signal detection antennas. As described in U.S. Pat. No. 6,752,768, which is hereby incorporated by reference in its entirety, a range of preprogrammed functionality may be incorporated into control module (12) to assist in taking tissue samples. Control module (12) controls and powers biopsy device (14) that is used with localization assembly (15). Biopsy device (14) is positioned and guided by localization fixture (16) attached to breast coil (18) that may be placed upon a gantry (not shown) of a MRI or other imaging machine.

In the present example, control module (12) is mechanically, electrically, and pneumatically coupled to biopsy device (14) so that components may be segregated that need to be spaced away from the strong magnetic field and the sensitive RF receiving components of a MRI machine. Cable management spool (20) is placed upon cable management attachment saddle (22) that projects from a side of control module (12). Wound upon cable management spool (20) is paired electrical cable (24) and mechanical cable (26) for communicating control signals and cutter rotation/advancement motions respectively. In particular, electrical and mechanical cables (24, 26) each have one end connected to respective electrical and mechanical ports (28, 30) in control module (12) and another end connected to holster portion (32) of biopsy device (14). Docking cup (34), which may hold holster portion (32) when not in use, is hooked to control module (12) by docking station mounting bracket (36). It should be understood that such components described above as being associated with control module (12) are merely optional.

Interface lock box (38) mounted to a wall provides tether (40) to lockout port (42) on control module (12). Tether (40) is uniquely terminated and of short length to preclude inadvertent positioning of control module (12) too close to a MRI machine or other machine. In-line enclosure (44) may register tether (40), electrical cable (24) and mechanical cable (26) to their respective ports (42, 28, 30) on control module (12).

Vacuum assist is provided by first vacuum line (46) that connects between control module (12) and outlet port (48) of vacuum canister (50) that catches liquid and solid debris.

Tubing kit (52) completes the pneumatic communication between control module (12) and biopsy device (14). In particular, second vacuum line (54) is connected to inlet port (56) of vacuum canister (50). Second vacuum line (54) divides into two vacuum lines (58, 60) that are attached to biopsy device (14). With biopsy device (14) installed in holster portion (32), control module (12) performs a functional check. Saline may be manually injected into biopsy device (14) or otherwise introduced to biopsy device (14), such as to serve as a lubricant and to assist in achieving a vacuum seal and/or for other purposes. Control module (12) actuates a cutter mechanism (not shown) in biopsy device (14), monitoring full travel of a cutter in biopsy device (14) in the present example. Binding in mechanical cable (26) or within biopsy device (14) may optionally monitored with reference to motor force exerted to turn mechanical cable (26) and/or an amount of twist in mechanical cable (26) sensed in comparing rotary speed or position at each end of mechanical cable (26).

Remote keypad (62), which is detachable from holster portion (32), communicates via electrical cable (24) to control panel (12) to enhance clinician control of biopsy device (14) in the present example, especially when controls that would otherwise be on biopsy device (14) itself are not readily accessible after insertion into localization fixture (16) and/or placement of control module (12) is inconveniently remote (e.g., 30 feet away). However, as with other components described herein, remote keypad (62) is merely optional, and may be modified, substituted, supplemented, or omitted as desired. In the present example, aft end thumbwheel (63) on holster portion (32) is also readily accessible after insertion to rotate the side from which a tissue sample is to be taken.

Of course, the above-described control module (12) is merely one example. Any other suitable type of control module (12) and associated components may be used. By way of example only, control module (12) may instead be configured and operable in accordance with the teachings of U.S. Pub. No. 2008/0228103, entitled "Vacuum Timing Algorithm for Biopsy Device," published Sep. 18, 2008, the disclosure of which is incorporated by reference herein. As another merely illustrative example, control module (12) may instead be configured and operable in accordance with the teachings of U.S. patent application Ser. No. 12/337,814, entitled "Control Module Interface for MRI Biopsy Device," filed Dec. 18, 2008, the disclosure of which is incorporated by reference herein. Alternatively, control module (12) may have any other suitable components, features, configurations, functionalities, operability, etc. Other suitable variations of control module (12) and associated components will be apparent to those of ordinary skill in the art in view of the teachings herein.

II. Localization Assembly

Localization assembly (15) of the present example comprises breast coil (18) and localization fixture (16). These components of localization assembly (15) are described further below.

Left and right parallel upper guides (64, 66) of localization framework (68) are laterally adjustably received respectively within left and right parallel upper tracks (70, 72) attached to under side (74) and to each side of a selected breast aperture (76) formed in patient support platform (78) of breast coil (18). Base (80) of breast coil (18) is connected by centerline pillars (82) that are attached to patient support platform (78) between breast apertures (76). Also, a pair of outer vertical support pillars (84, 86) on each side spaced about a respective breast aperture (76) respectively define lateral recess (88) within which localization fixture (16) resides.

It should be appreciated that the patient's breasts hang pendulously respectively into breast apertures (76) within lateral recesses (88) in the present example. For convenience, herein a convention is used for locating a suspicious lesion by Cartesian coordinates within breast tissue referenced to localization fixture (16) and to thereafter selectively position an instrument, such as needle (90) of probe (91) that is engaged to holster portion (32) to form biopsy device (14). Of course, any other type of coordinate system or targeting techniques may be used. To enhance hands-off use of biopsy system (10), especially for repeated re-imaging within the narrow confines of a closed bore MRI machine, biopsy system (10) may also guide obturator (92) encompassed by cannula (94). Depth of insertion is controlled by depth stop device (95) longitudinally positioned on either needle (90) or cannula (94). Alternatively, depth of insertion may be controlled in any other suitable fashion.

This guidance is specifically provided by a lateral fence in the present example, depicted as grid plate (96), which is received within laterally adjustable outer three-sided plate bracket (98) attached below left and right parallel upper guides (64, 66). Similarly, a medial fence with respect to a medial plane of the chest of the patient, depicted as medial plate (100), is received within inner three-sided plate bracket (102) attached below left and right parallel upper guides (64, 66) close to centerline pillars (82) when installed in breast coil (18). To further refine the insertion point of the instrument (e.g., needle (90) of probe (91), obturator/cannula (92, 94), etc.), guide cube (104) may be inserted into grid plate (96).

In the present example, the selected breast is compressed along an inner (medial) side by medial plate (100) and on an outer (lateral) side of the breast by grid plate (96), the latter defining an X-Y plane. The X-axis is vertical (sagittal) with respect to a standing patient and corresponds to a left-to-right axis as viewed by a clinician facing the externally exposed portion of localization fixture (16). Perpendicular to this X-Y plane extending toward the medial side of the breast is the Z-axis, which typically corresponds to the orientation and depth of insertion of needle (90) or obturator/cannula (92, 94) of biopsy device (14). For clarity, the term Z-axis may be used interchangeably with "axis of penetration", although the latter may or may not be orthogonal to the spatial coordinates used to locate an insertion point on the patient. Versions of localization fixture (16) described herein allow a non-orthogonal axis of penetration to the X-Y axis to a lesion at a convenient or clinically beneficial angle.

It should be understood that the above-described localization assembly (15) is merely one example. Any other suitable type of localization assembly (15) may be used, including but not limited to localization assemblies (15) that use a breast coil (18) and/or localization fixture (16) different from those described above. Other suitable components, features, configurations, functionalities, operability, etc. for a localization assembly (15) will be apparent to those of ordinary skill in the art in view of the teachings herein.

III. Biopsy Device

As shown in FIG. 1, one version of biopsy device (14) may comprise holster portion (32) and probe (91). Exemplary holster portion (32) was discussed previously in the above section addressing control module (12). The following paragraphs will discuss probe (91) and associated components and devices in further detail.

Figure 4:
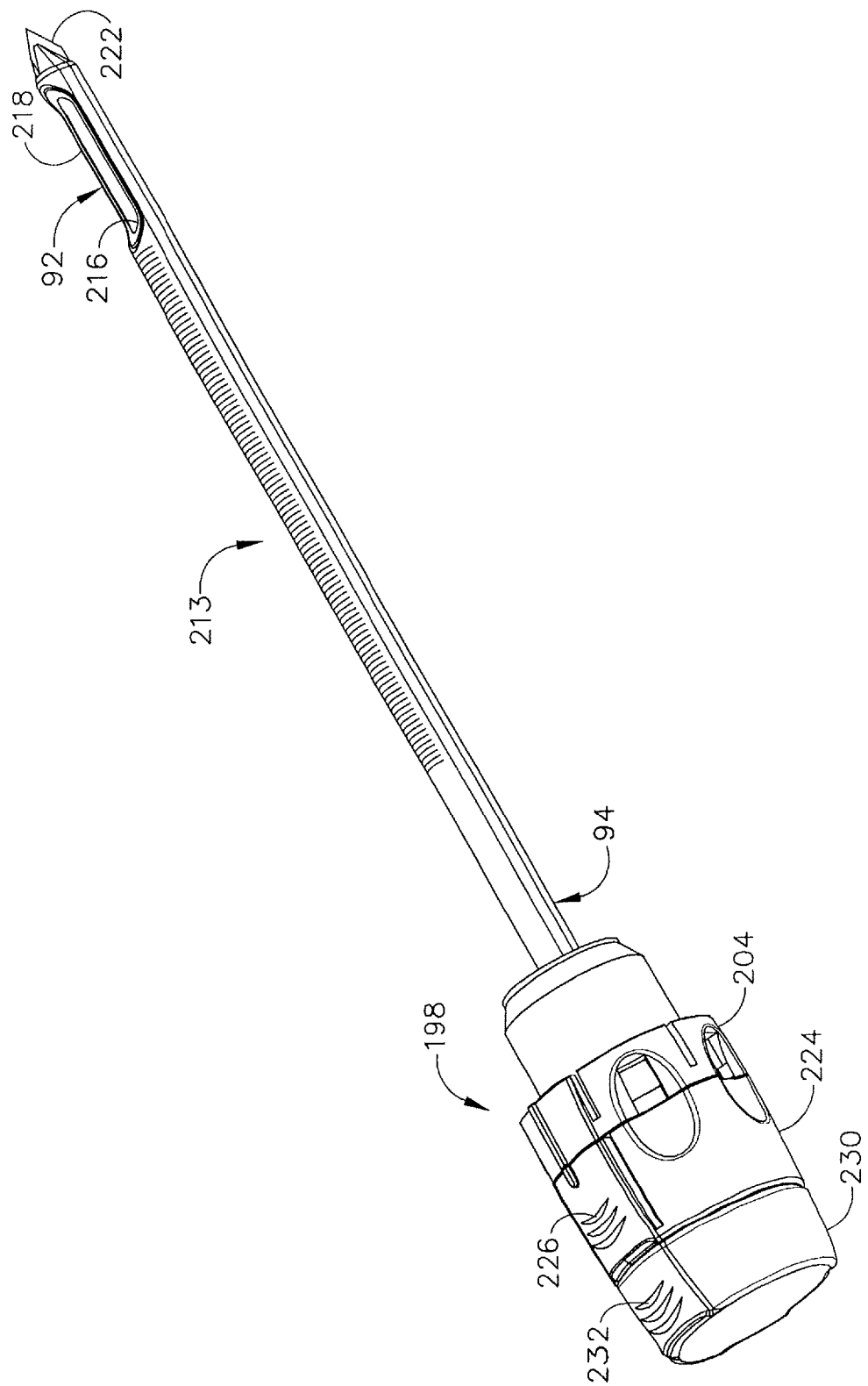
FIG. 4 is a perspective view of the obturator and cannula of the biopsy system of FIG. 1.
Figure 5:
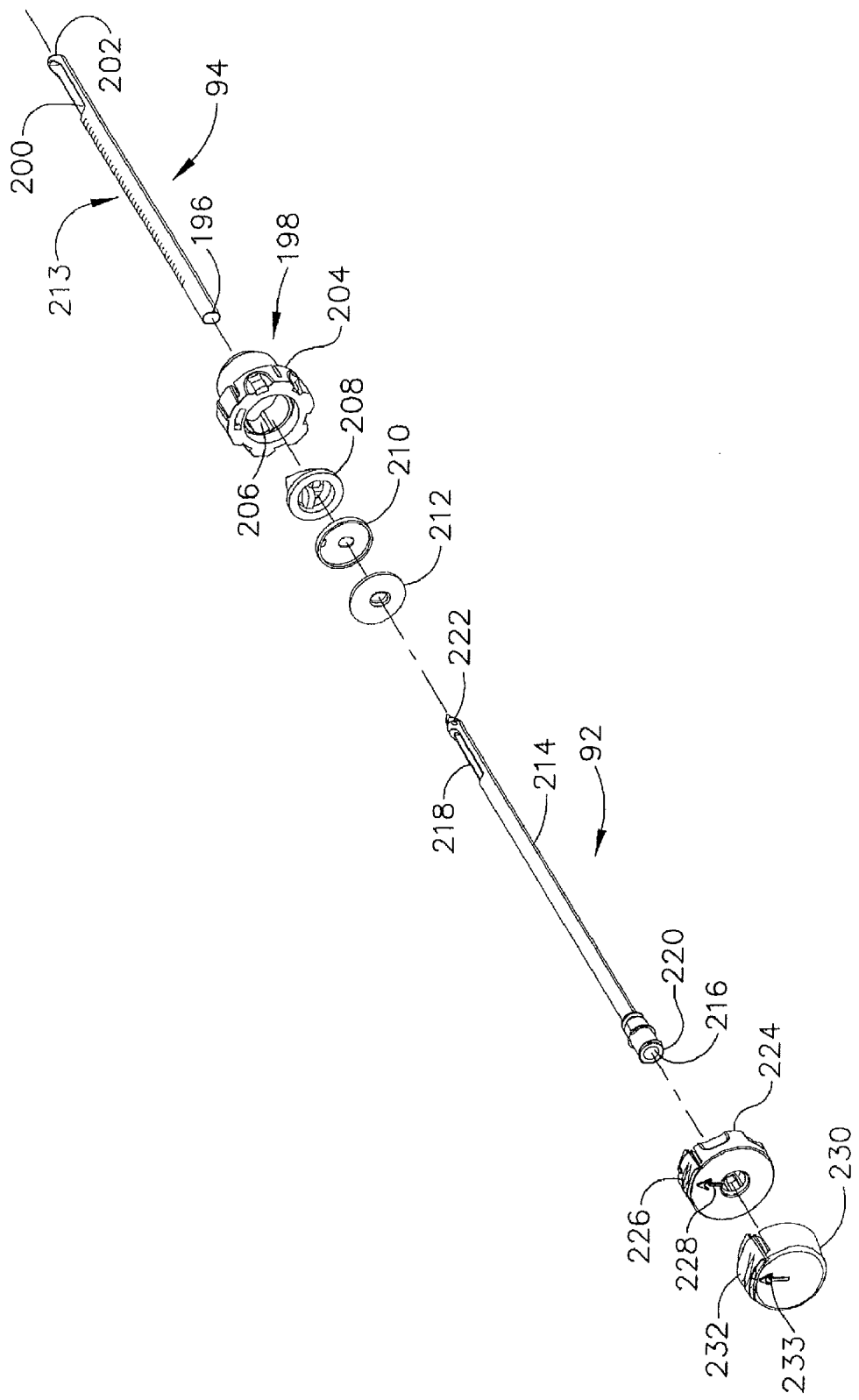
FIG. 5 is an exploded perspective view of the obturator and cannula of FIG. 4.
Figure 7:
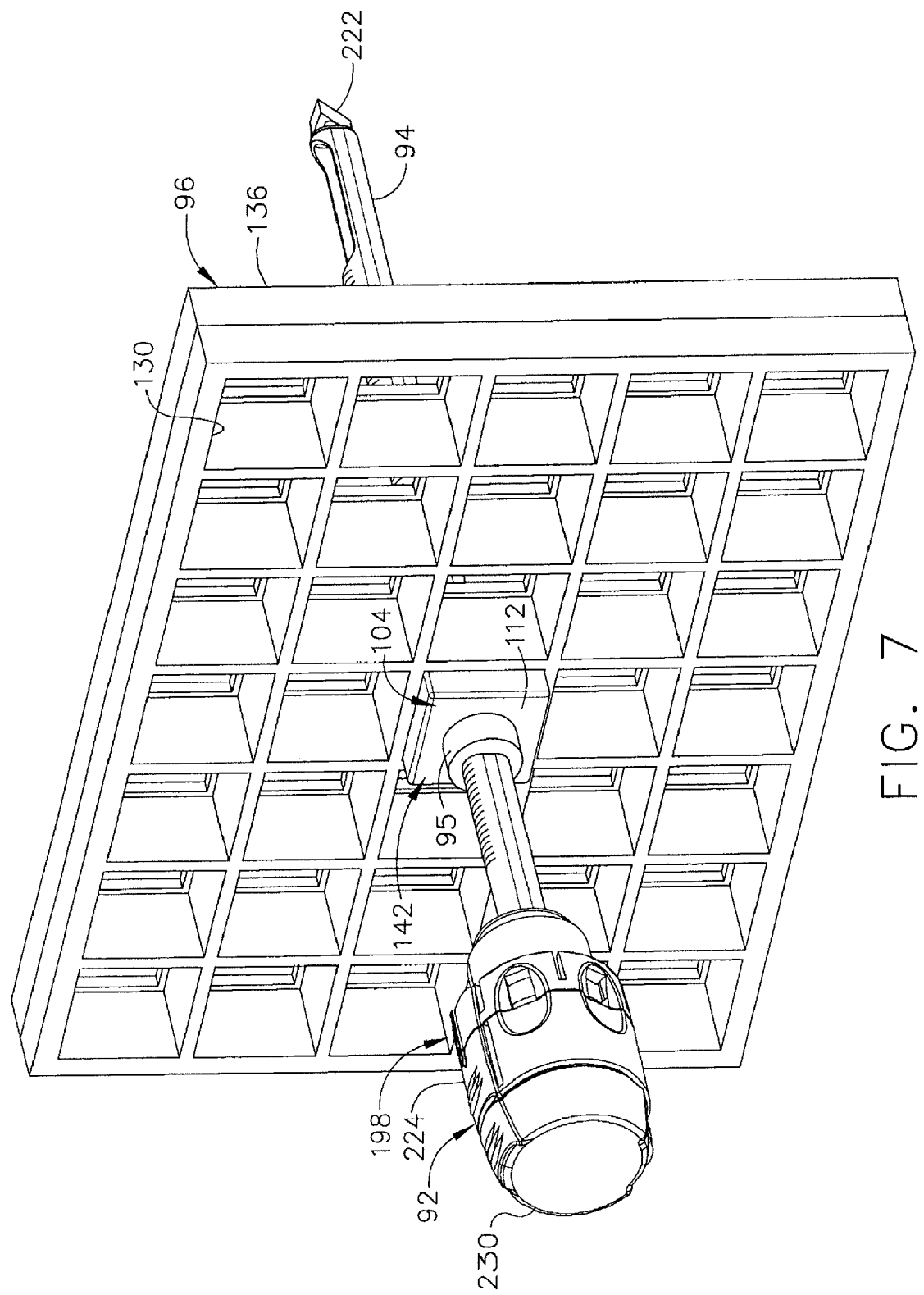
FIG. 7 is a perspective view of the obturator and cannula of FIG. 4 with a depth stop device of FIG. 1 inserted through the guide cube and grid plate of FIG. 6.

In the present example, cannula (94) and obturator (92) are associated with probe (91). In particular, and as shown in FIGS. 4, 5, and 7, obturator (92) is slid into cannula (94) and the combination is guided through guide cube (104) to the biopsy site within the breast tissue. Obturator (92) is then withdrawn from cannula (94), then needle (90) of probe (91) is inserted in cannula (94), and then biopsy device (14) is operated to acquire one or more tissue samples from the breast via needle (90).

Cannula (94) of the present example is proximally attached to cylindrical hub (198) and cannula (94) includes lumen (196) and lateral aperture (200) proximate to open distal end (202). Cylindrical hub (198) has exteriorly presented thumbwheel (204) for rotating lateral aperture (200). Cylindrical hub (198) has interior recess (206) that encompasses duckbill seal (208), wiper seal (210) and seal retainer (212) to provide a fluid seal when lumen (196) is empty and for sealing to inserted obturator (92). Longitudinally spaced measurement indicia (213) along an outer surface of cannula (94) visually, and perhaps physically, provide a means to locate depth stop device (95) of FIG. 1.

Obturator (92) of the present example incorporates a number of components with corresponding features. Hollow shaft (214) includes fluid lumen (216) that communicates between imageable side notch (218) and proximal port (220). Hollow shaft (214) is longitudinally sized to extend, when fully engaged with cannula (94), piercing tip (222) out of distal end (202) of cannula (94). Obturator thumbwheel cap (224) encompasses proximal port (220) and includes locking feature (226), which includes visible angle indicator (228), that engages cannula thumbwheel (204) to ensure that imageable side notch (218) is registered to lateral aperture (200) in cannula (94). Obturator seal cap (230) may be engaged proximally into obturator thumbwheel cap (224) to close fluid lumen (216). Obturator seal cap (230) of the present example includes locking or locating feature (232) that includes visible angle indicator (233) that corresponds with visible angle indicator (228) on obturator thumbwheel cap (224), which may be fashioned from either a rigid, soft, or elastomeric material. In FIG. 7, guide cube (104) has guided obturator (92) and cannula (94) through grid plate (96).

While obturator (92) of the present example is hollow, it should be understood that obturator (92) may alternatively have a substantially solid interior, such that obturator (92) does not define an interior lumen. In addition, obturator (92) may lack side notch (218) in some versions. Other suitable components, features, configurations, functionalities, operability, etc. for an obturator (92) will be apparent to those of ordinary skill in the art in view of the teachings herein. Likewise, cannula (94) may be varied in a number of ways. For instance, in some other versions, cannula (94) has a closed distal end (202). As another merely illustrative example, cannula (94) may have a closed piercing tip (222) instead of obturator (92) having piercing tip (222). In some such versions, obturator (92) may simply have a blunt distal end; or the distal end of obturator (92) may have any other suitable structures, features, or configurations. Other suitable components, features, configurations, functionalities, operability, etc. for a cannula (94) will be apparent to those of ordinary skill in the art in view of the teachings herein. Furthermore, in some versions, one or both of obturator (92) or cannula (94) may be omitted altogether. For instance, needle (90) of probe (91) may be directly inserted into a guide cube (104), without being inserted into guide cube (104) via cannula (94).

Another component that may be used with probe (91) (or needle (90)) is depth stop (95). Depth stop may be of any suitable configuration that is operable to prevent cannula (94) and obturator (92) (or needle (90)) from being inserted further than desired. For instance, depth stop (95) may be positioned on the exterior of cannula (94) (or needle (90)), and may be configured to restrict the extent to which cannula (94) is inserted into a guide cube. It should be understood that such restriction by depth stop (95) may further provide a limit on the depth to which the combination of cannula (94) and obturator (92) (or needle (90)) may be inserted into the patient's breast. Furthermore, it should be understood that such restriction may establish the depth within the patient's breast at which biopsy device (14) acquires one or more tissue samples after obturator (92) has been withdrawn from cannula (94) and needle (90) has been inserted in cannula (94). Exemplary depth stops (95) that may be used with biopsy system (10) are described in U.S. Pub. No. 2007/0255168, entitled "Grid and Rotatable Cube Guide Localization Fixture for Biopsy Device," published Nov. 1, 2007, and incorporated by reference herein as mentioned previously.

In the present example, and as noted above, biopsy device (14) includes a needle (90) that may be inserted into cannula (94) after the combination of cannula (94) and obturator (92) has been inserted to a desired location within a patient's breast and after obturator (92) has been removed from cannula (94). Needle (90) of the present example comprises a lateral aperture (not shown) that is configured to substantially align with lateral aperture (200) of cannula (94) when needle (90) is inserted into lumen (196) of cannula (94). Probe (91) of the present example further comprises a rotating and translating cutter (not shown), which is driven by components in holster (32), and which is operable to sever tissue protruding through lateral aperture (200) of cannula (94) and the lateral aperture of needle (90). Severed tissue samples may be retrieved from biopsy device (14) in any suitable fashion.

By way of example only, biopsy device (14) may be configured and operable in accordance with the teachings of U.S. Pub. No. 2008/0228103, entitled "Vacuum Timing Algorithm For Biopsy Device," published Sep. 18, 2008, the disclosure of which is incorporated by reference herein. As another merely illustrative example, biopsy device (14) may be configured and operable in accordance with the teachings of U.S. patent application Ser. No. 12/337,874, entitled "Mechanical Tissue Sample Holder Indexing Device," filed Dec. 18, 2008, the disclosure of which is incorporated by reference herein. As another merely illustrative example, biopsy device (14) may be configured and operable in accordance with the teachings of U.S. patent application Ser. No. 12/337,674, entitled "Biopsy Device with Sliding Cutter Cover," filed Dec. 18, 2008, the disclosure of which is incorporated by reference herein. By way of example only, cannula (94) may be replaced with any of the detachable needles described in U.S. patent application Ser. No. 12/337,674, entitled "Biopsy Device with Sliding Cutter Cover." As another merely illustrative example, biopsy device (14) may be configured and operable in accordance with the teachings of U.S. patent application Ser. No. 12/337,911, entitled "Biopsy Device with Discrete Tissue Chambers," filed Dec. 18, 2008, the disclosure of which is incorporated by reference herein. As another merely illustrative example, biopsy device (14) may be configured and operable in accordance with the teachings of U.S. patent application Ser. No. 12/337,942, entitled "Biopsy Device with Central Thumbwheel," filed Dec. 18, 2008, the disclosure of which is incorporated by reference herein. Alternatively, biopsy device (14) may have any other suitable components, features, configurations, functionalities, operability, etc. Other suitable variations of biopsy device (14) and associated components will be apparent to those of ordinary skill in the art in view of the teachings herein IV. Guide Cubes Guide cubes described below are generally adapted for use with a localization assembly (15) as described above. Numerous features of merely exemplary guide cubes will be discussed in the paragraphs that follow.

A. Guide Cubes Generally

In some versions, guide cubes may comprise a body defined by one or more edges and faces. The body may include one or more guide holes or other types of passages that extend between faces of the guide cube and that may be used to guide an instrument such as a biopsy device (14) or a portion of a biopsy device (14) (e.g., needle (90) of biopsy device (14), a combination of cannula (94) and obturator (92), etc.). Guide cubes may be rotatable about one, two, or three axes to position the one or more guide holes or passages of the guide cube into a desired position.

Figure 8:
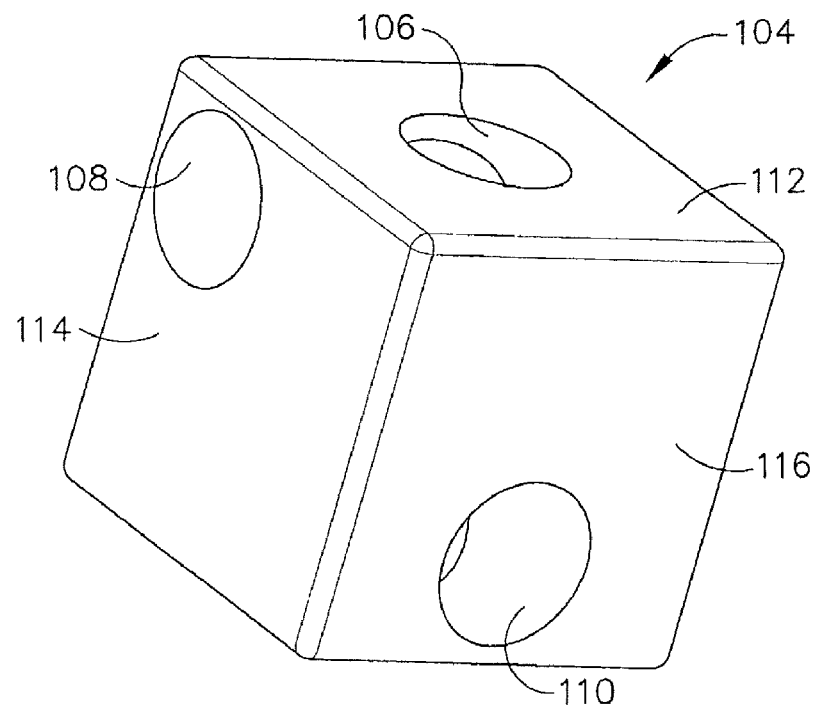
FIG. 8 is a perspective view of the guide cube of the biopsy system of FIG. 1.
Figure 9:
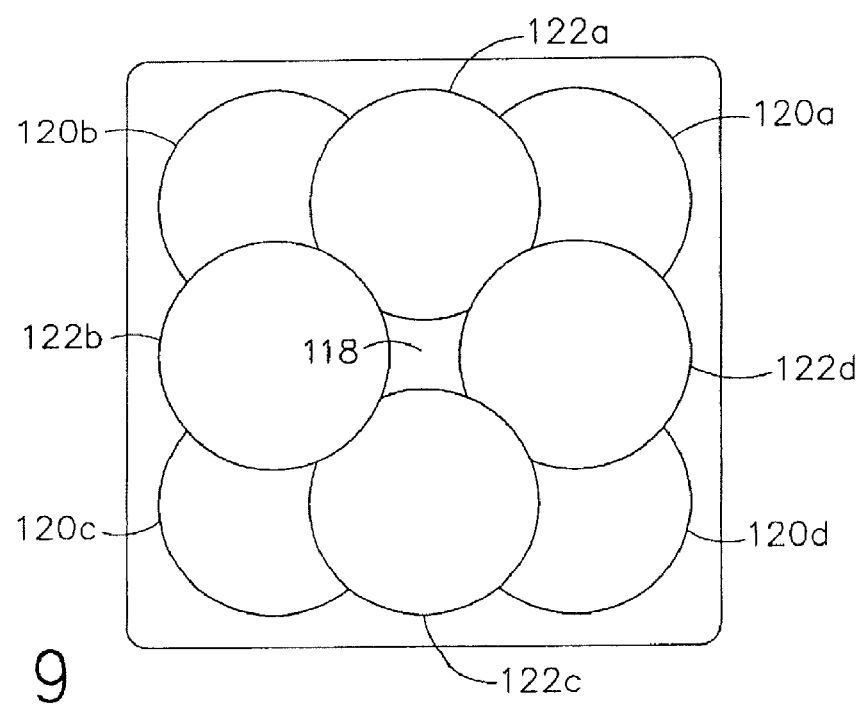
FIG. 9 is a diagram of nine guide positions achievable by rotating the guide cube of FIG. 8.

Referring now to FIG. 8, guide cube (104), includes central guide hole (106), corner guide hole (108), and off-center guide hole (110) that pass orthogonally to one another between respective opposite pairs of faces (112, 114, 116). By selectively rotating guide cube (104) in two axes, one pair of faces (112, 114, 116) may be proximally aligned to an unturned position and then the selected proximal face (112, 114, 116) optionally rotated a quarter turn, half turn, or three-quarter turn. Thereby, one of nine guide positions (118, 120a-120d, 122a-122d) may be proximally exposed as depicted in FIG. 9. More specifically, central guide hole (106) may provide for guide position (118), corner guide hole (108) may provide for guide positions (120a-120d), and off-center guide hole (110) may provide for guide positions (122a-122d).

Figure 6:
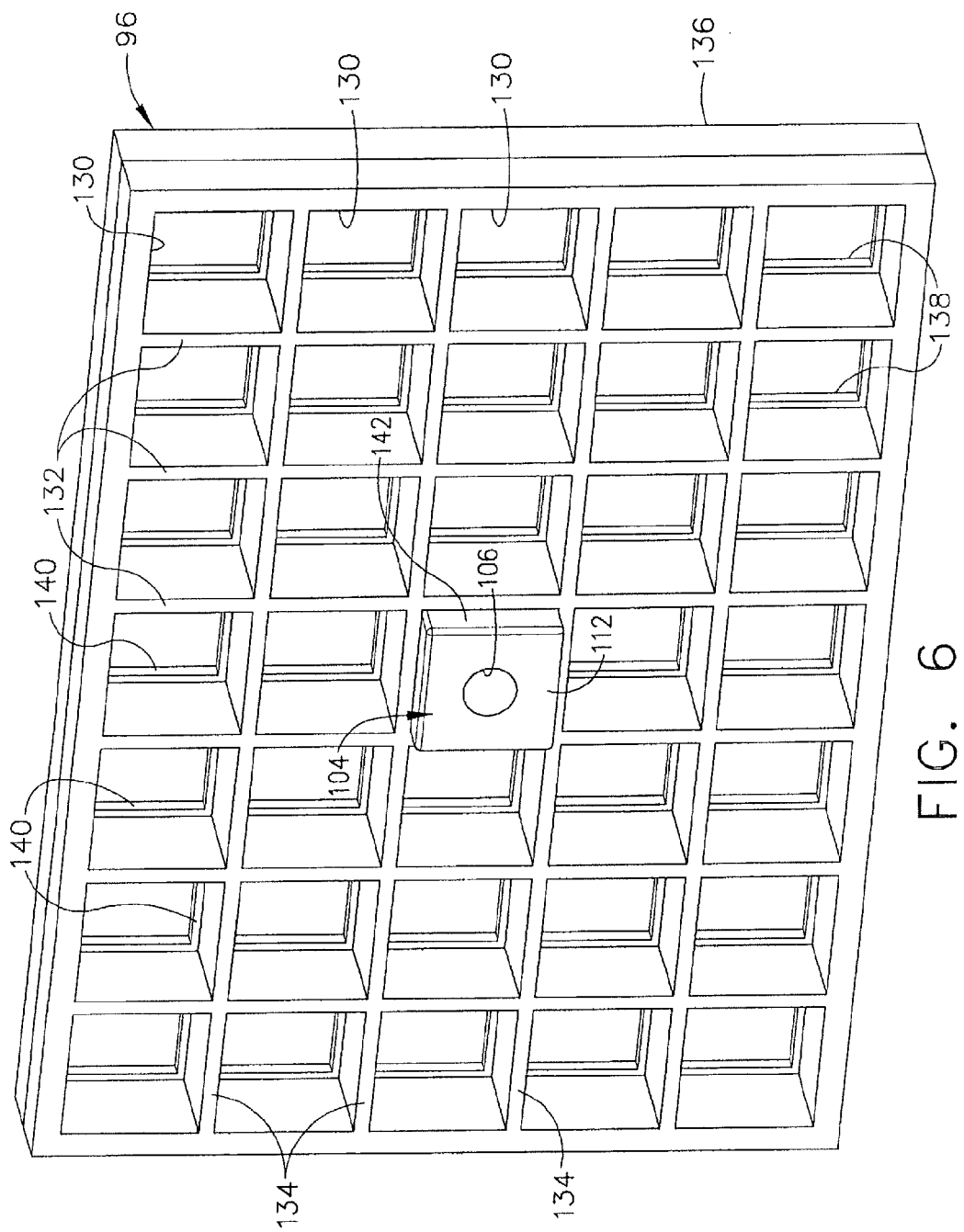
FIG. 6 is a perspective view of the guide cube inserted into the grid plate of the localization assembly of FIG. 1.

In FIG. 6, two-axis rotatable guide cube (104) is sized for insertion from a proximal side into one of a plurality of square recesses (130) in grid plate (96), which are formed by intersecting vertical bars (132) and horizontal bars (134). Guide cube (104) is prevented from passing through grid plate (96) by backing substrate (136) attached to a front face of grid plate (96). Backing substrate (136) includes respective square opening (138) centered within each square recess (130), forming lip (140) sufficient to capture the front face of guide cube (104), but not so large as to obstruct guide holes (104, 106, 108). The depth of square recesses (130) is less than guide cube (104), thereby exposing a proximal portion (142) of guide cube (104) for seizing and extraction from grid plate (96). It will be appreciated by those of ordinary skill in the art based on the teachings herein that backing substrate (136) of grid plate (96) may be omitted altogether in some versions. In some such versions without backing substrate (136) other features of a guide cube, as will be discussed in more detail below, may be used to securely and removably fit a guide cube within a grid plate. However, such other features may also be used in combination with a grid plate having backing substrate (136), such as grid plate (96), instead of partially or wholly omitting backing substrate (136).

B. Self-Grounding Guide Cubes

Figure 10:
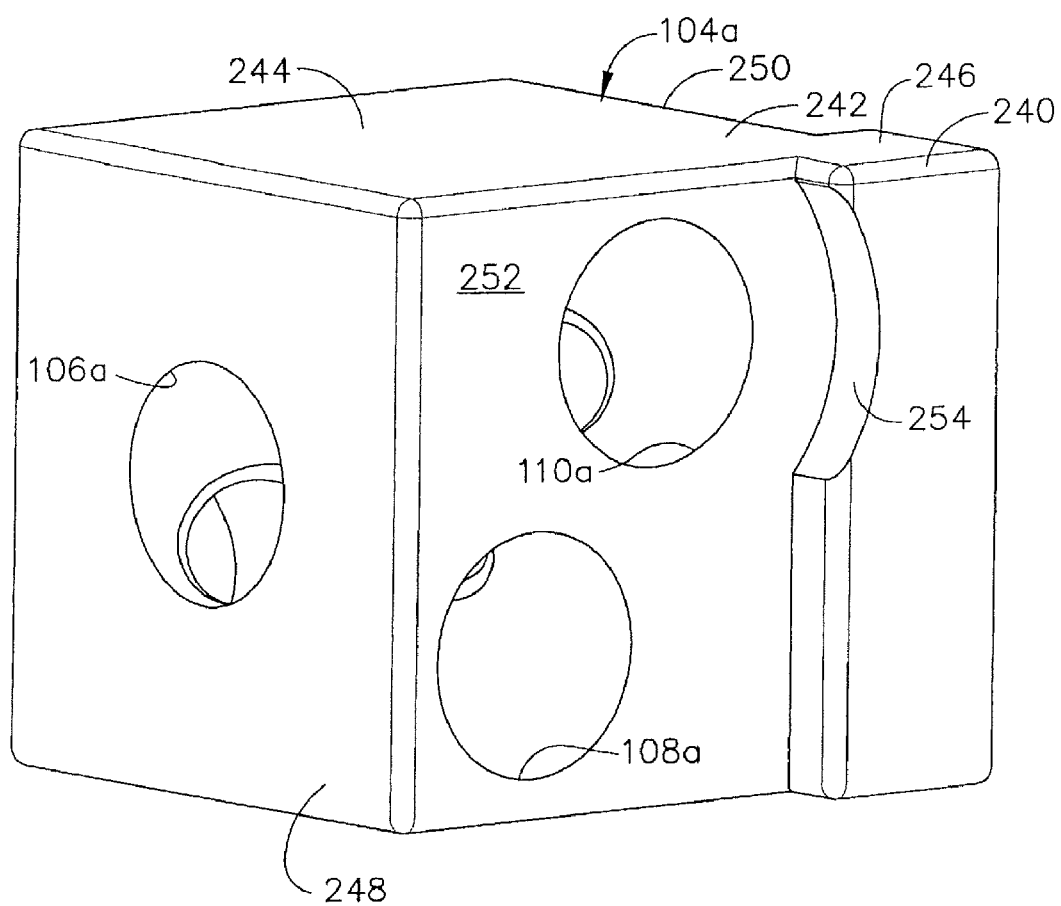
FIG. 10 is a perspective view of another guide cube for the biopsy system of FIG. 1 with a self-grounding feature.
Figure 11:
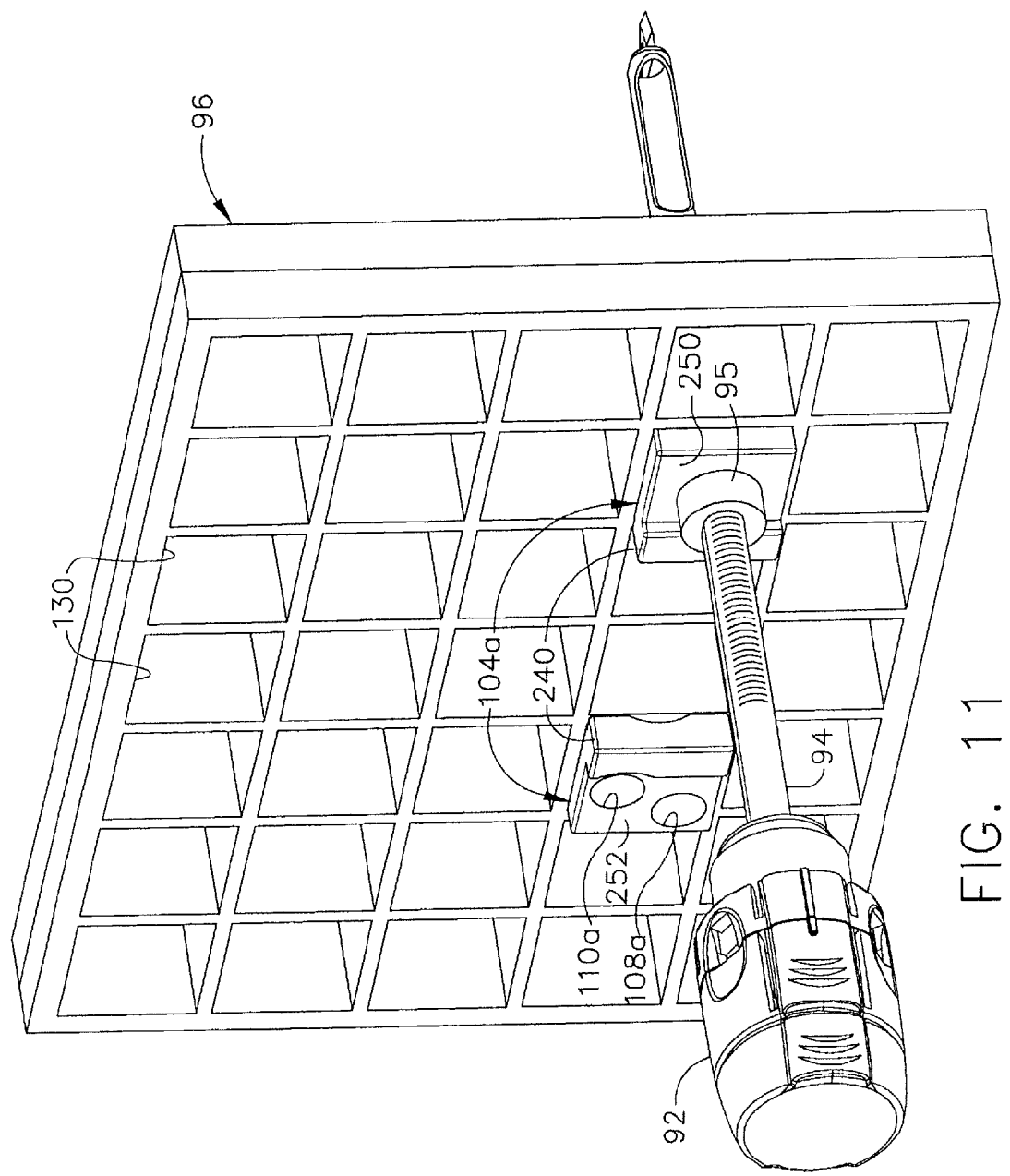
FIG. 11 is a perspective view of the obturator and cannula of FIG. 1 inserted into one of two guide cubes of FIG. 10 inserted into the grid plate of FIG. 1.

In FIG. 10, guide cube (104a) has self-grounding by means of added rectangular prism (240) which has a shared edge with cubic portion (242) of guide cube (104a). When viewed orthogonally to the shared cube edge, larger square face (244) of cubic portion (242) overlaps with smaller square face (246) of rectangular prism (240). As shown in FIG. 11, rectangular prism (240) allows proximal exposure of one of two adjacent faces (250, 252) of guide cube (104a) and then turning each to one of four quarter-turn rotational positions. In the illustrative version, first face (250) has central guide hole (106a) and second face (252) has corner guide hole (108a), and off-center guide hole (110a). Radial recess (254) is formed in rectangular prism (240) to allow grounding of depth stop device (95) against face (252) when off-center guide hole (110a) is used.

Figure 12:
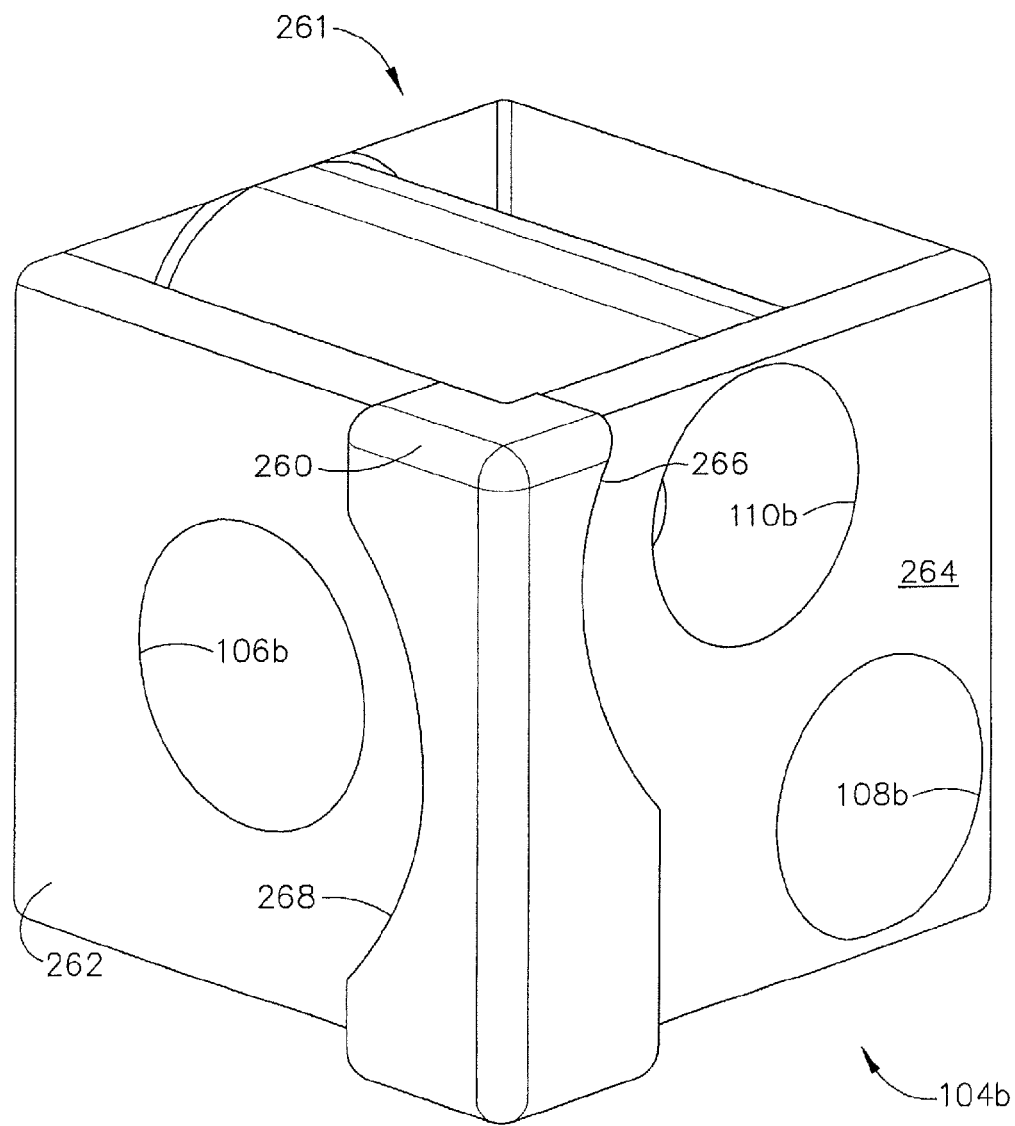
FIG. 12 is a perspective view of another guide cube having an open top and bottom with another self-grounding feature.

In FIG. 12, guide cube (104b) has self-grounding by means of added rectangular prism (260) that protrudes from two faces (262, 264) of guide cube (104b). Rectangular prism (260) allows proximal exposure of one of two adjacent faces (262, 264) of guide cube (104b) and then turning each to one of four quarter-turn rotational positions. In the illustrative version, first face (262) has central guide hole (106b) and second face (264) has corner guide hole (108b) and off-center guide hole (110b). First radial recess (266) is formed in rectangular prism (260) to allow grounding of depth stop device (95) against face (264) when off-center guide hole (110b) is used. Second radial recess (268) is formed in rectangular prism (260) to allow grounding of depth stop device (95) against face (262) when central guide hole (106b) is used. As discussed in greater detail below, guide cube (104b) may have open top (261) and/or an open bottom (not shown) defined by the faces of guide cube (104b) as depicted in the illustrated version.

Figure 13:
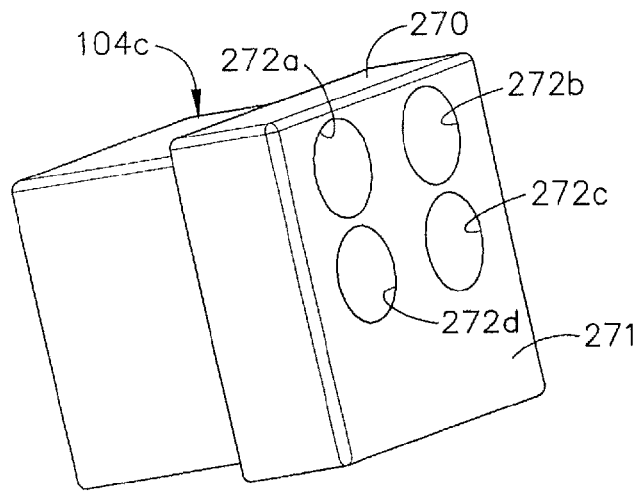
FIG. 13 is a rear perspective view of another guide cube with another self-grounding feature.
Figure 14:
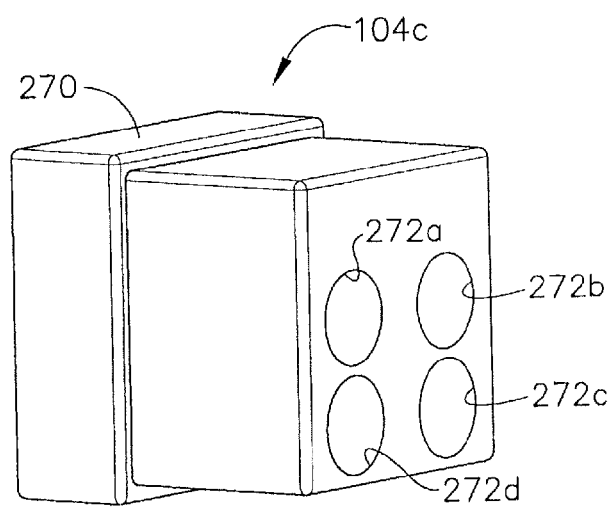
FIG. 14 is a front perspective view of the guide cube of FIG. 13.
Figure 15:
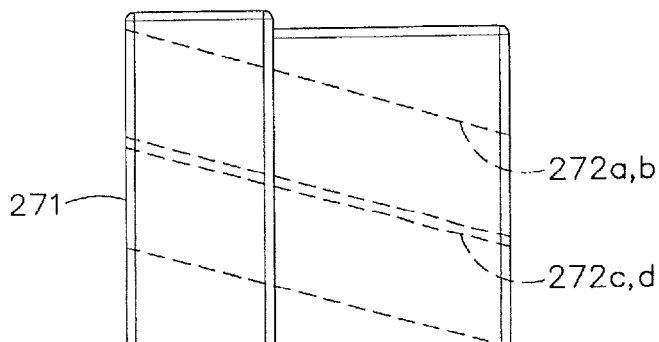
FIG. 15 is a right side view of the guide cube of FIG. 13 with angled, parallel guide holes depicted in phantom.

In FIGS. 13-15, guide cube (104c) has proximal enlarged hat portion (270) about proximal face (271) that grounds against selected square recess (130), such as in grid plate (96), and allows rotation about one axis to one of four quarter-turn positions. Four angled guide holes (272a, 272b, 272c, 272d) allow accessing not only an increased number of insertion points within selected square recess (130) but also a desired angle of penetration rather than being constrained to a perpendicular insertion. It will be appreciated based on the teachings herein that while angled guide holes may be used in some versions, orthogonal guide holes may be used instead of or in addition to angled guide holes in other versions.

C. Eccentric Lock

Figure 16A:
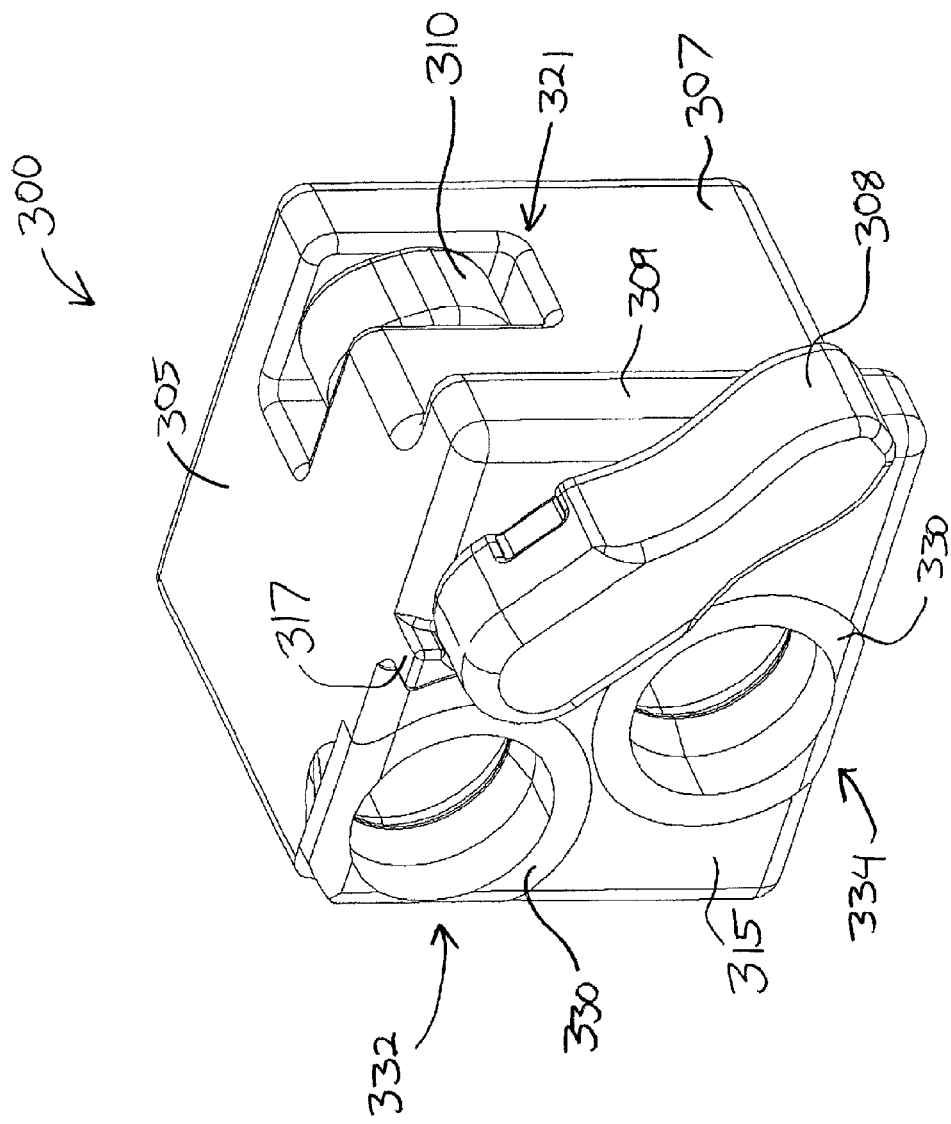
FIG. 16A is a front perspective view of another guide cube having a lever actuated eccentric elastomeric lock with elastomeric inserts within the guide holes, with the lock in an unlocked position.
Figure 16C:
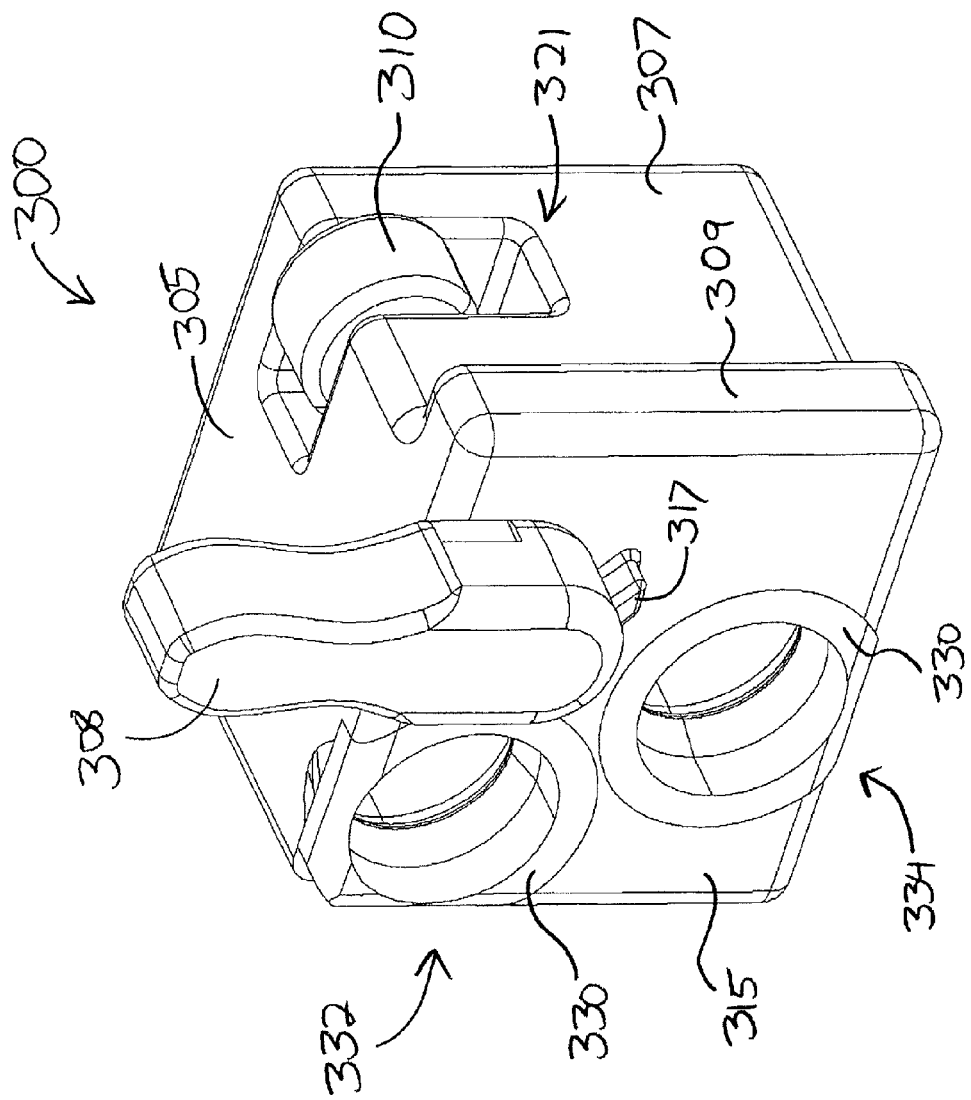
FIG. 16C is a front perspective view of the guide cube of FIG. 16A, with the lock in a locked position.
Figure 16D:
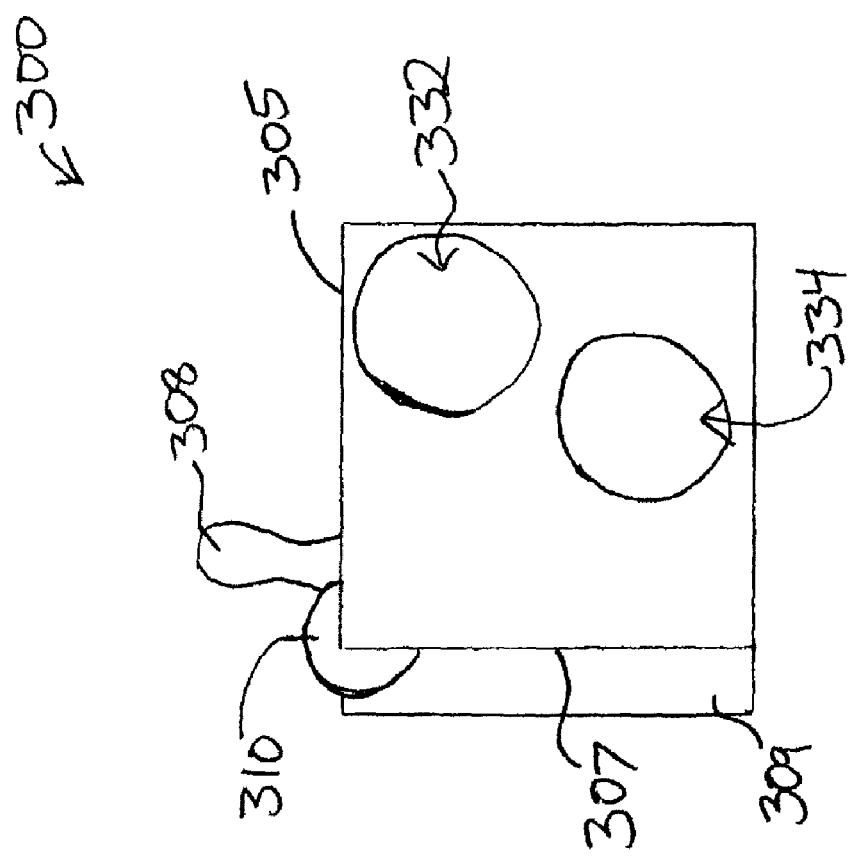
FIG. 16D is a rear elevational view of the guide cube of FIG. 16C, with the lock in the locked position.

As shown in FIGS. 16A-19E, guide cubes (300, 302, 304, 306) may include an eccentric lock. Generally, the eccentric lock may include an actuating member and a locking member, among other types of components. Referring to FIGS. 16A-16D, the eccentric lock of some versions may include lever (308) as the actuating member and wheel (310) as the locking member. Lever (308) and wheel (310) may be connected by shaft (311) as shown in FIG. 20. Shaft (311) may extend through wheel (310) and be positioned off-center (e.g., such that shaft (311) does not extend through the center of wheel (310)) such that an eccentric orientation is achieved. When lever (308) is rotated, a corresponding rotation is imparted to shaft (311). The rotation of shaft (311) imparts a corresponding rotation to the wheel (310). With the eccentric or non-coaxial orientation, as wheel (310) rotates, the outermost portions of wheel (310) may extend from guide cube (300). In particular, FIGS. 16A-16B show wheel (310) in an unlocked position, whereby wheel (310) does not extend outwardly past the planes defined by sides (305, 307) of guide cube (300). FIGS. 16C-16D show wheel (310) in a locked position after lever (308) has been rotated, whereby wheel (310) extends outwardly past the planes defined by sides (305, 307) of guide cube (300). The extension of wheel (310) shown in FIGS. 16C-16D allows wheel (310) to contact and resiliently bear against one or more inner portions of a selected square recess (130) of grid plate (96), thereby substantially locking guide cube (300) into a secure position.

Wheel (310) may be constructed wholly or partially of an elastomeric material such that wheel (310) compresses to some degree when wheel (310) contacts an inner portion of a selected square recess (130) of grid plate (96). Such compression action of wheel (310) may permit guide cube (300) to be used with a variety of available grid plates, possibly having various sized openings for receiving a guide cube such as guide cube (300). Based on the teachings herein, those of ordinary skill in the art will appreciate that several elastomeric materials may be suitable for use with wheel (310). By way of example only, suitable elastomeric materials may include thermosetting plastics that may require vulcanization, thermoplastic elastomers (e.g. Santoprene™ among others), natural rubber, synthetic rubbers (e.g. ethylene propylene diene M-class—EPDM—among others), and other polymers having suitable elastic properties. It should be understood that the elastomeric properties of wheel (310) may provide increased friction between guide cube (300) and grid plate (96) when wheel (310) has been rotated to the locked position shown in FIGS. 16C-16D.

Figure 18A:
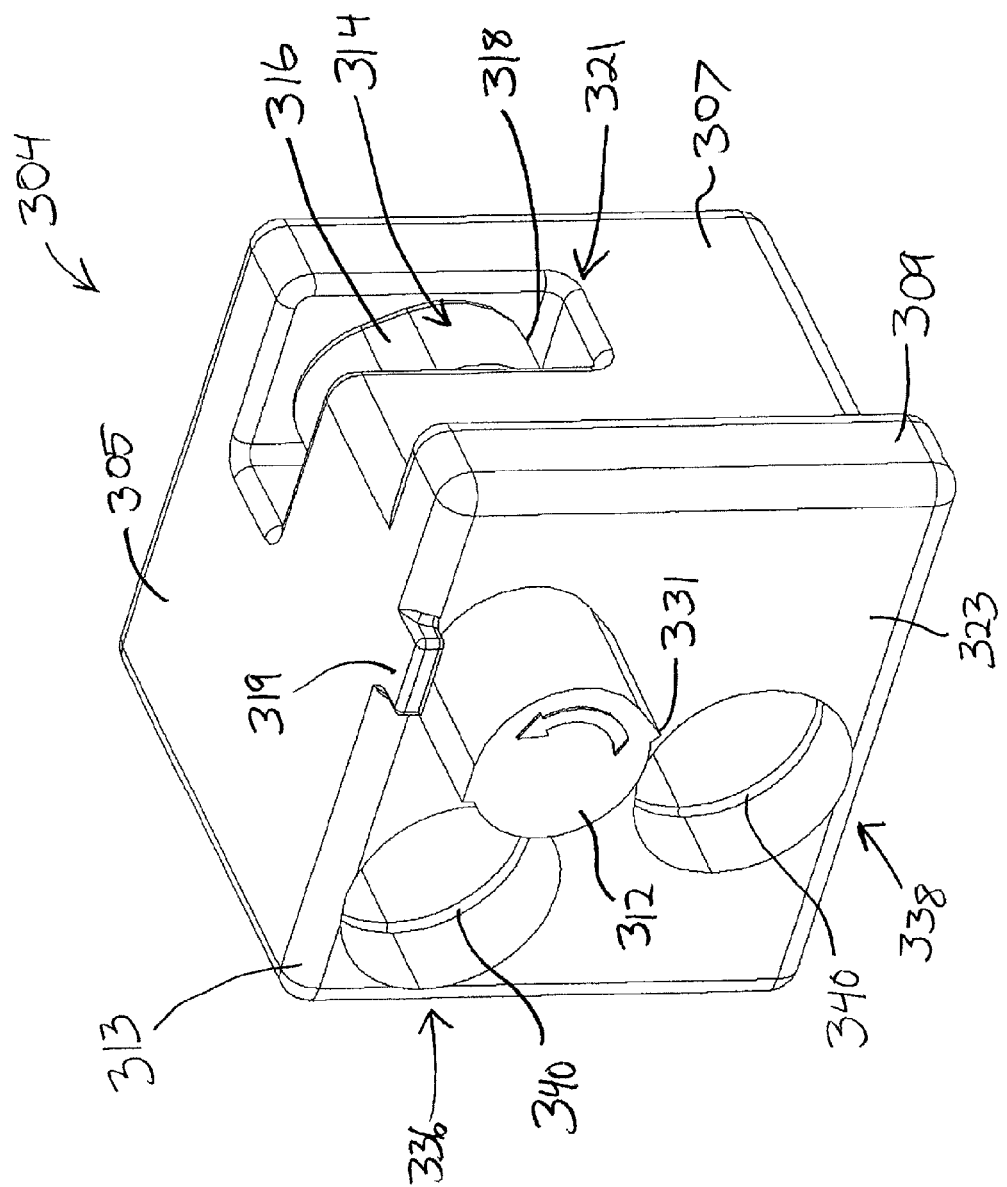
FIG. 18A is a front perspective view of another guide cube having a knob actuated eccentric elastomeric lock with elastomeric retaining rings within the guide holes, with the lock in an unlocked position.
Figure 18C:
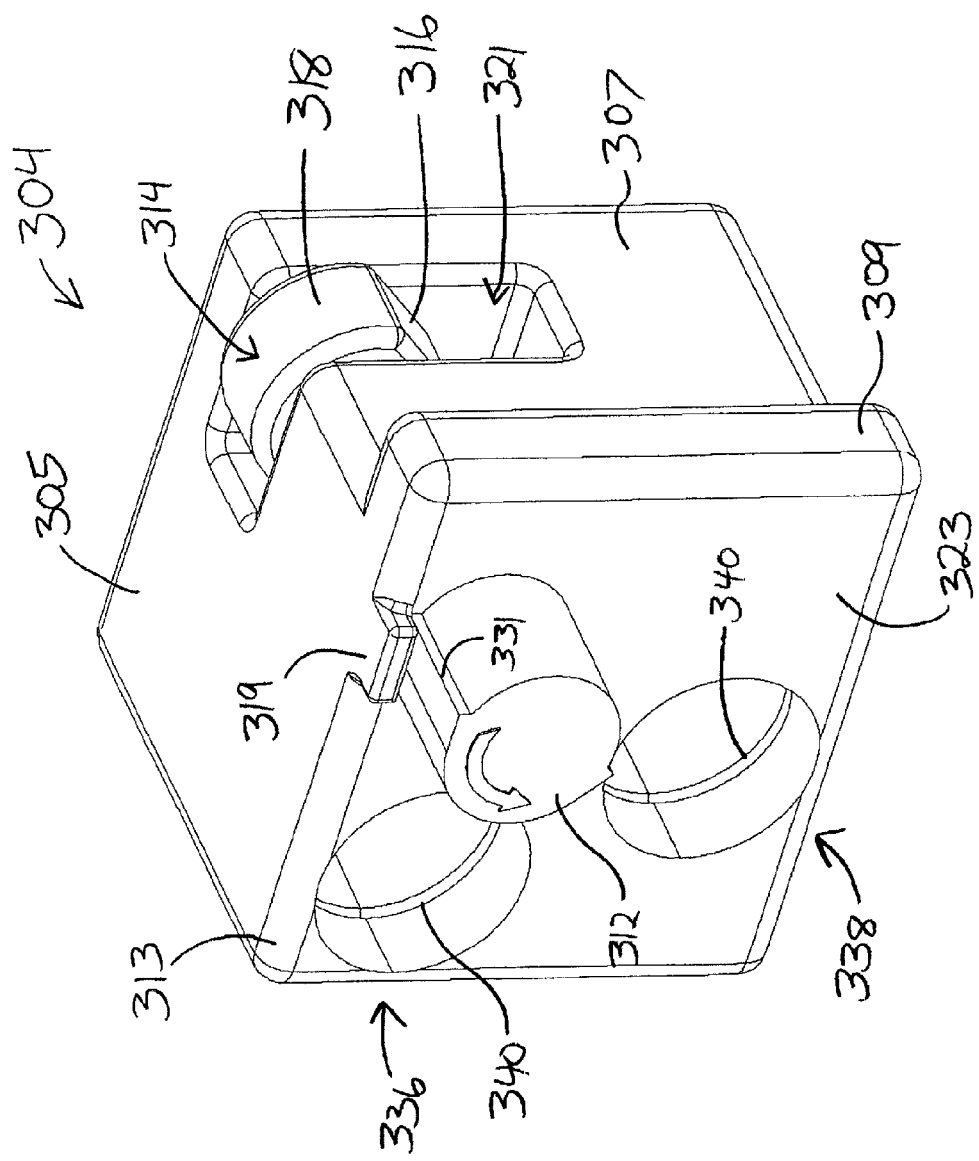
FIG. 18C is a front perspective view of the guide cube of FIG. 18A, with the lock in a locked position.
Figure 21:
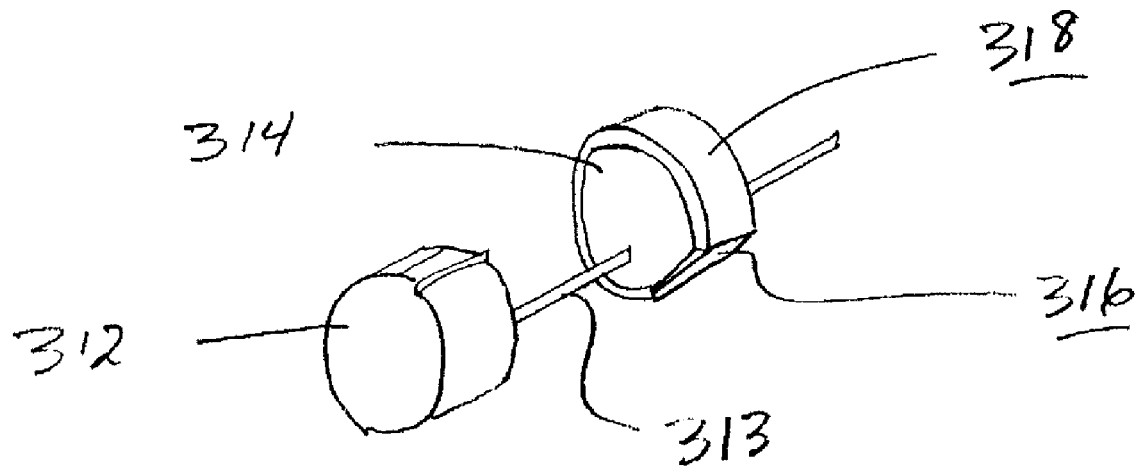
FIG. 21 is a front perspective view of the eccentric lock of FIG. 18 without the guide cube shown.

In FIGS. 18A-18D, another version shows guide cube (304) having knob (312) as the actuating member and wheel (314) as the locking member. Knob (312) and wheel (314) may be connected by a shaft (313) as shown in FIG. 21. Shaft (311) may extend through wheel (314) and be positioned off-center (e.g., such that shaft (311) does not extend through the center of wheel (310)) such that an eccentric orientation is achieved. Additionally, wheel (314) may include flat surface portion (316) and curved surface portion (318). Knob (312) may be rotated by hand or by using a separate tool. When knob (312) is rotated, a corresponding rotation is imparted to shaft (313). The rotation of shaft (313) imparts a corresponding rotation to the wheel (314). As wheel (314) rotates, the outermost portions of wheel (314) may extend from guide cube (304), in part due to the eccentric orientation, and in part due to the shape of wheel (314). In particular, FIGS. 18A-18B show wheel (314) in an unlocked position, whereby wheel (314) does not extend outwardly past the planes defined by sides (305, 307) of guide cube (304). FIGS. 18C-18D show wheel (314) in a locked position after knob (312) has been rotated, whereby wheel (314) extends outwardly past the planes defined by sides (305, 307) of guide cube (304). The extension of wheel (314) shown in FIGS. 18C-18D allows wheel (314) to contact and resiliently bear against one or more inner portions of a selected square recess (130) of grid plate (96), thereby substantially locking guide cube (304) into a secure position.

In some versions of guide cube (304), wheel (314) has two perpendicularly adjacent flat surface portions (316), such that these two perpendicularly adjacent flat surface portions (316) are substantially parallel to and/or substantially flush with corresponding outer surfaces (305, 307) of the body of guide cube (304) when wheel (314) is rotated to an unlocking position. When knob (312) is rotated to rotate wheel (314) to a locking position, one or both of the flat surface portions (316) may be rotated into notch (321) of guide cube (304), with a newly exposed curved surface portion (318) of wheel (314) engaging the inner portion of a selected square recess (130) of grid plate (96) to lock guide cube (304) into a secure position. In some such versions of guide cube (304), the axis of knob (312), shaft (313), and wheel (314) may be coaxial rather than eccentric.

Wheel (314) may be constructed wholly or partially of an elastomeric material such that wheel (314) compresses to some degree when wheel (314) contacts an inner portion of a selected square recess (130) of grid plate (96). Such compression action of wheel (314) may permit guide cube (304) to be used with a variety of available grid plates, possibly having various sized openings for receiving a guide cube such as guide cube (304). Based on the teachings herein, those of ordinary skill in the art will appreciate that several elastomeric materials may be suitable for use with wheel (314). By way of example only, suitable elastomeric materials may include thermosetting plastics that may require vulcanization, thermoplastic elastomers (e.g. Santoprene™ among others), natural rubber, synthetic rubbers (e.g. ethylene propylene diene M-class—EPDM—among others), and other polymers having suitable elastic properties. It should be understood that the elastomeric properties of wheel (314) may provide increased friction between guide cube (304) and grid plate (96) when wheel (314) has been rotated to the locked position shown in FIGS. 18C-18D.

Regarding the mechanism of extension due to the shape of wheel (314), curved surface portion (318) may be positioned further from shaft (313) compared to flat surface portion (316) as shown in FIG. 21. Thus rotating wheel (314) causes wheel (314) to extend in the direction that flat surface portion (316) initially faced because upon rotation, curved surface portion (318) will move into the rotational position that flat surface portion (316) previously occupied. Since curved surface portion (318) may be positioned further from shaft (313) compared to flat surface portion (316), curved surface portion (318) will protrude further than did flat surface portion (316) when in the same rotational position that flat surface portion (316) previously occupied.

It will be appreciated based on the teachings herein that in other versions, the extension of wheel (314) may be achieved by the shape of wheel (314) alone, without using an eccentric relationship. In some such versions, knob (312) and wheel (314) may be connected by shaft (313) in a coaxial relationship. However, the shape of wheel (314), having flat surface portion (316) and curved surface portion (318) as described above, provides suitable extension of wheel (314) upon rotation as described above.

Referring again to FIGS. 16A-16D and 18A-18D, during operation of the eccentric locking mechanisms of the present example, wheel (310, 314) may extend from guide cubes (300, 304) so as to contact one or more sidewalls of selected square recess (130) of grid plate (96). For instance, in some versions where the eccentric lock is engaged, wheels (310, 314) extend upward (extending past the plane defined by side (305)) and laterally (extending past the plane defined by side (307)) from guide cubes (300, 304) respectively. In such versions, the outermost portions of wheels (310, 314) may contact an upper portion and a side portion of the sidewall interior of selected square recess (130) of grid plate (96). In still some other versions, when the eccentric lock is engaged, wheels (310, 314) may extend from guide cubes (300, 304) such that the outermost portions of wheels (310, 314) contact only one portion of the sidewall interior of selected square recess (130) of grid plate (96), such as either an upper portion or a side portion of a sidewall interior. Based on the teachings herein, those of ordinary skill in the art will appreciate that having locking components contact multiple surfaces of a grid plate (96) may assist in securing a guide cube within a grid plate (96); however, sufficient securing may be achieved with such locking components contacting only one surface of a grid plate (96).

Still in other versions, multiple eccentric locks may be used. For instance, a single guide cube (300, 304) may have multiple wheels (310, 314). Furthermore one or more levers (308), knobs (312), or other actuating members may be configured to operate one, more, or all wheels (310, 314). By way of example only, some versions of multi-wheel guide cubes may provide simultaneous operation of all wheels with a single lever or knob. Some other versions of multi-wheel guide cubes may provide more than one lever or knob, with each lever or knob controlling a single corresponding wheel or particular group of wheels. Other ways in which multiple wheels may be implemented in a guide cube will be apparent to those of ordinary skill in the art in view of the teachings herein.

Figure 17A:
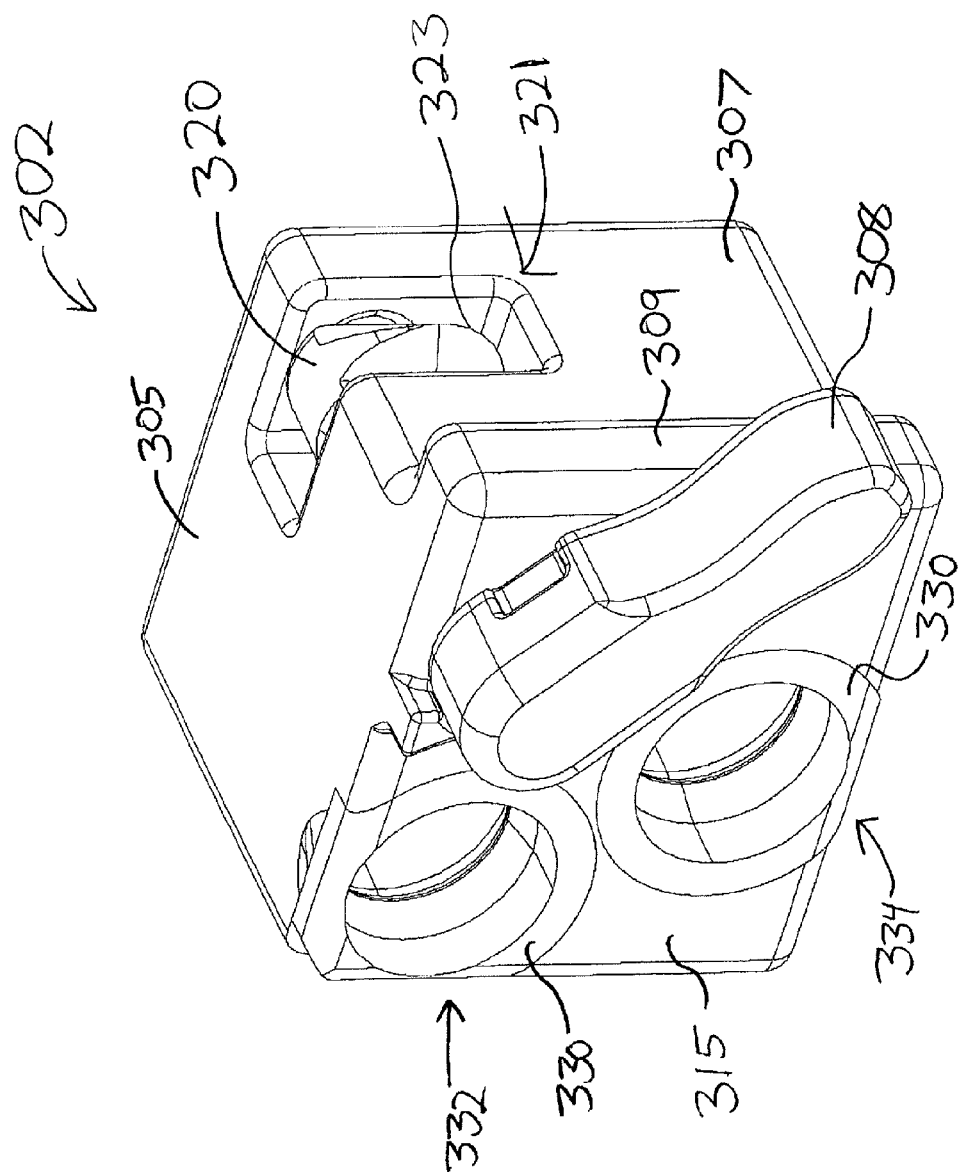
FIG. 17A is a front perspective view of another guide cube having a lever actuated eccentric ceramic lock with elastomeric inserts within the guide holes, with the lock in an unlocked position.
Figure 17D:
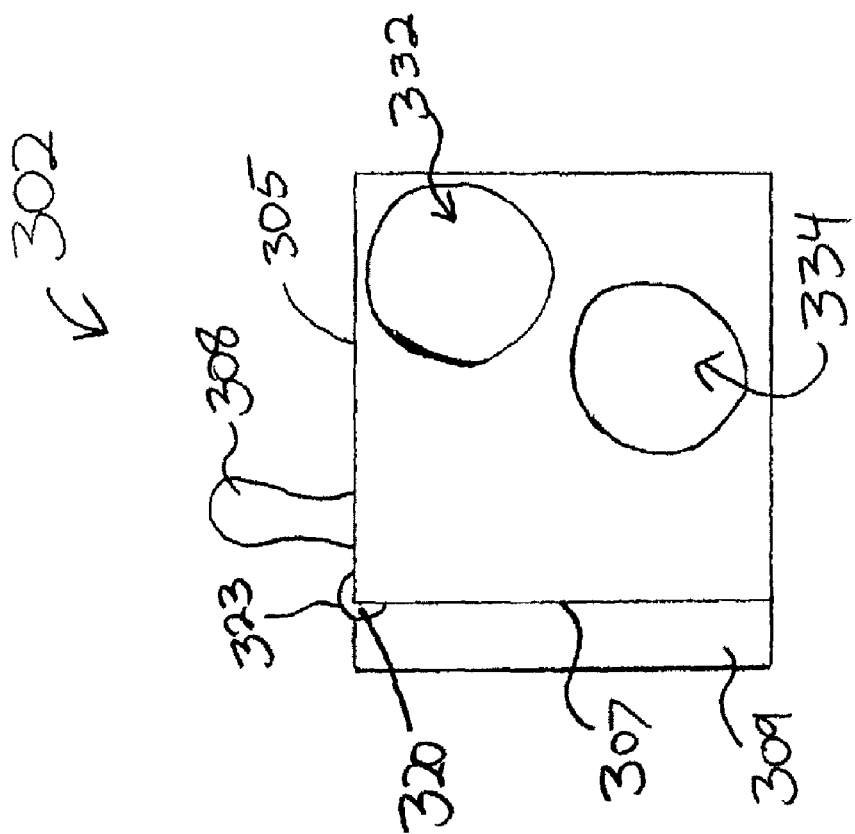
FIG. 17D is a rear elevational view of the guide cube of FIG. 17C, with the lock in the locked position.

Referring now to FIGS. 17A-17D, another version shows guide cube (302) having an eccentric locking mechanism using lever (308) as the actuating member for locking member (320). Locking member (320) may be constructed of various rigid materials compatible with the various imaging technologies discussed above. In some versions, locking member (320) is comprised of ceramic. In other versions, locking member (320) may be comprised of plastic, titanium, and/or other suitable materials, including combinations thereof When locking member (320) is used, certain features may be incorporated to permit guide cube (302) to be compatible with various available grid plates. For instance, in some versions, at least a portion of locking member (320) may have a cone shape or frustoconical shape as shown in FIGS. 17A-17D. In particular, locking member (320) may present a cutting edge (323) that may be selectively retracted or extended from notch (321) based on the rotational position of lever (308). In some versions, locking member (320) is eccentrically mounted on a shaft extending from lever (308), such that the eccentric mounting of locking member (320) provides selective extension or retraction of cutting edge (323) relative to sides (305, 307) upon rotation of lever (308). In some other versions, locking member (320) is coaxially mounted on a shaft extending from lever (308), yet the shape of locking member (320) itself provides selective extension or retraction of cutting edge (323) relative to sides (305, 307) upon rotation of lever (308). FIGS. 17A-17B show locking member (320) in an unlocked position, whereby locking member (320) does not extend outwardly past the planes defined by sides (305, 307) of guide cube (302). FIGS. 17C-17D show locking member (320) in a locked position after lever (308) has been rotated, whereby cutting edge (323) extends outwardly past the planes defined by sides (305, 307) of guide cube (302). The extension of cutting edge (323) shown in FIG. 17B allows cutting edge (323) to "dig into" one or more inner portions of a selected square recess (130) of grid plate (96), thereby substantially locking guide cube (302) into a secure position.

In operation, guide cube (302) may be placed within selected square recess (130) of grid plate (96). Lever (308) is then rotated, and this action rotates a connected shaft (not shown). The shaft connects with the cone-shaped locking member (320) such that the shaft and locking member (320) are non-coaxial, providing an eccentric relationship. As the shaft rotates, the shaft causes the locking member (320) to rotate. The eccentric relationship between the shaft and the locking member (320) causes the cutting edge (323) of locking member (320) to extend outwardly from guide cube (302) when rotated. At this point, the locking member (320) may engage with one or more sidewall interiors of selected square recess (130) of grid plate (96) as discussed above with respect to FIGS. 16A-16D and 18A-18D. However, rather than compressing, cutting edge (323) of locking member (320) may lightly score or displace a small amount of material on the inner sidewall of square recess (130) to achieve positive engagement with grid plate (96). In other words, and particularly where locking member (320) is made of a material (e.g., ceramic, etc.) that is harder than the material of which grid plate (96) is formed (e.g., plastic, etc.), locking member (320) may essentially "dig into" grid plate (96) to anchor guide cube (302) within square recess (130). To remove an anchored guide cube (302) from grid plate (96), a user may simply rotate lever (308) in the opposite direction to disengage locking member (320) from the inner sidewall of square recess (130).

In some other versions, locking member (320) may alternatively engage with one or more outer frame portions of grid plate (96) that define square recess (130) and/or with slots formed in sidewall interiors. Where locking member (320) engages a frame portion, the conical shape of locking member (320) may permit secure engagement with various grid plates that may have frame components of various dimensions. Still in other versions where grid plate (96) includes backing substrate (136), guide cube (302) may be sized to fit within selected square opening (138) of backing substrate (136). In such versions, locking member (320) may then be configured to engage backing substrate (136) itself when locking member (320) is actuated. Where locking member (320) engages backing substrate (136), the conical shape of locking member (320) may permit secure engagement with various grid plate having backing substrates of various dimensions. In some other versions, guide cube (302) may be sized such that backing substrate (136) blocks guide cube (302) from over-insertion in grid plate (96). In some such versions, locking member (320) may then be configured to engage one or more sidewall interiors of selected square recess (130) of grid plate (96) as discussed above.

In some other versions of guide cube (302) having locking member (320), locking member (320) may be removable such that other locking members of different sizes can be used in place of locking member (320). Since locking member (320) may be rigid, matching the size of the locking member used with the particular opening in the grid plate may assist in providing a secure fit of guide cube (302) within the grid plate. While part of locking member (320) has a frustoconical shape to provide cutting edge (323) in the present example, it should be understood that locking member (320) may have a variety of other configurations. By way of example only, a cutting edge (323) may be provided by some configuration other than a frustoconical shape. For instance, locking member (320) may have one or more spurs or hook-shaped members protruding from part of the outer perimeter of locking member (320). Still other suitable structures and configurations that may be incorporated into locking member (320), to "dig into" grid plate (96) or otherwise, will be apparent to those of ordinary skill in the art in view of the teachings herein.

It should also be understood that locking member (320) may be used with various size grid plates by configuring lever (308) to lock when locking member (320) contacts a surface of the grid plate (96). In some such versions, lever (308) may move from a first position to a second position when locking member (320) moves from a position of non-contact with the grid plate (96) to a position contacting the grid plate. Lever (308) may then further move from the second position to a third, locked, position when continued force is put on lever (308) after locking member (320) has contacted the grid plate (96). It should be appreciated that the features of lever (308) described in this version may also be adapted to work with other versions of guide cubes described above. Similarly, knob (312) may be adapted to incorporate the same or similar locking features as described in this version.

As shown in FIGS. 16A-18D, to accommodate an eccentric lock as described above, guide cubes (300, 302, 304) may be configured with notch (321) to house components of the eccentric lock. For example, notch (321) may provide adequate void space in guide cubes (300, 302, 304) to retain wheel (310, 314) or locking member (320) as shown. It should be appreciated that while notch (321) may house some components of the eccentric lock, notch (321) may be positioned in guide cube (300, 302, 304) in such a manner as to not interfere with the guide holes of guide cube (300, 302, 304). While notch (321), wheel (310, 314), and locking member (320) are all shown as being located along one corner edge of guide cube (300, 302, 304), it should be understood that these components may be located elsewhere, including but not limited to along a face of guide cube (300, 302, 304) (e.g., between corner edges of guide cube (300, 302, 304)). In some versions, guide cubes (300, 302, 304) may also have a passageway (not shown) for housing shafts (311, 313). Based on the teachings herein, those of ordinary skill in the art will appreciate that various other guide cube modifications may be made to accommodate an eccentric lock as described herein.

Referring still to FIGS. 16A-18D, guide cubes (300, 302, 304) may be configured with additional components that are operable with lever (308) or knob (312). In some versions, braking member (317) is used to arrest lever (308) at a desired rotational position. As shown in FIGS. 16A, 16C, 17A, and 17C, lever (308) and braking member (317) may be located on a proximal face (315) of guide cube (300, 302, 304). When lever (308) is rotated clockwise, lever (308) will eventually contact braking member (317), and braking member (317) will prevent further rotation of lever (308). Similarly, when lever (308) is rotated counter-clockwise, lever (308) will eventually contact braking member (317), and braking member (317) will prevent further rotation of lever (308). In the present example, braking member (317) restricts rotation of lever (308) to a range of approximately 90°, though any other suitable rotation restriction range may be provided.

As shown in FIGS. 18A and 18C, guide cube (304) may include projection (319), which may be located along a top edge (313) of guide cube (304) and extends proximally from guide cube (304). Knob (312) may be positioned on proximal face (323) of guide cube (304) and knob (312) may include protruding tips (331). In particular, tips (331) are located on radially opposing sides of knob (312) in this example, though it should be understood that just one tip (331) or no tips (331) may be provided in other versions. When knob (312) is rotated counter-clockwise, knob (312) will rotate until protruding tip (331) contacts projection (319) in this example. Thus, projection (319) and tip (331) together prevent any further counter-clockwise rotation of knob (312). Similarly, when knob (312) is rotated clockwise, knob (312) will rotate until protruding tip (331) contacts projection (319) in this example. Thus, projection (319) and tip (331) together prevent any further clockwise rotation of knob (312). In other words, projection (319) and tip (331) together restrict rotation of knob (312) to a range of approximately 180°, though any other suitable rotation restriction range may be provided. Based on the teachings herein, those of ordinary skill in the art will appreciate that various other modifications may be made to control the rotation of actuating members of an eccentric lock as described herein.

In some versions, braking member (317) and/or projection (319) provides a detent mechanism, in addition to or in lieu of restricting the degree of rotation of lever (308) or knob (312). For instance, when lever (308) or knob (312) has been rotated to a position where wheel (310, 314) or locking member (320) is suitably engaged with the sidewall interior of grid plate (96), braking member (317) and/or projection (319) may provide resistance to further rotation of lever (308) or knob (312) in either direction. Similarly, braking member (317) and/or projection (319) may provide tactile and/or audible feedback to indicate that lever (308) or knob (312) has been rotated to a position where wheel (310, 314) or locking member (320) is suitably engaged with the sidewall interior of grid plate (96). In addition or in the alternative, braking member (317) and/or projection (319) may provide resistance to initial rotation of lever (308) or knob (312), before wheel (310, 314) or locking member (320) has been rotated to suitably engage with the sidewall interior of grid plate (96).

Referring now to FIGS. 19A-19E, guide cube (306) is another version having an eccentric lock. Guide cube (306) comprises lever (322) connected to a shaft (not shown), which is further connected to connection member (324). Connection member (324) may be formed of an elastomeric material, of a ceramic material, and/or of any other suitable material or combination of materials. In some versions, at least a portion of connection member (324) may have a cone shape or frustoconical shape as shown in FIGS. 19A-19D, and may be formed of a hard material such as ceramic. In particular, connection member (324) may present a cutting edge (329) that may be selectively retracted or extended relative to sides (317, 326) of guide cube (306) based on the rotational position of lever (322). In some versions, connection member (324) is eccentrically mounted on a shaft extending from lever (322), such that the eccentric mounting of connection member (324) provides selective extension or retraction of cutting edge (329) relative to sides (317, 326) upon rotation of lever (322). In some other versions, connection member (324) is coaxially mounted on a shaft extending from lever (322), yet the shape of connection member (324) itself provides selective extension or retraction of cutting edge (329) relative to sides (317, 326) upon rotation of lever (322).

Figure 19B:
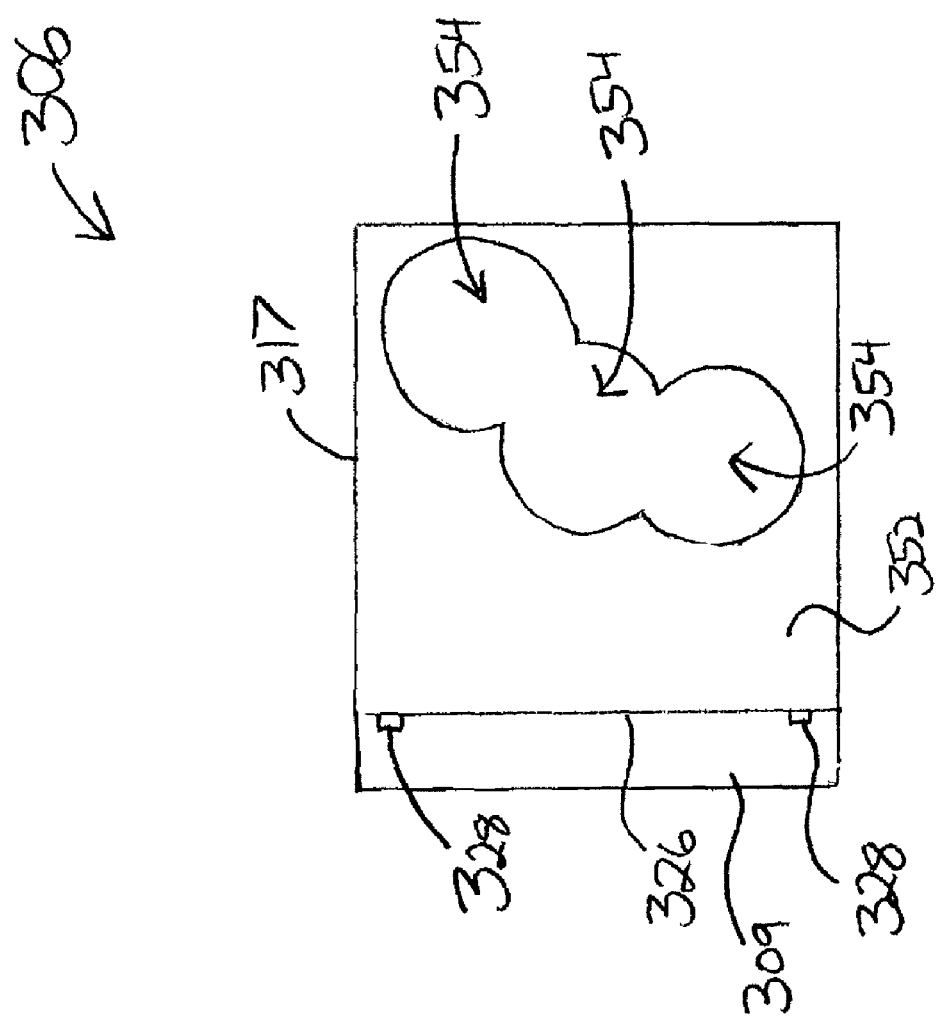
FIG. 19B is a rear elevational view of the guide cube of FIG. 19A, with the lock in the unlocked position.
Figure 19C:
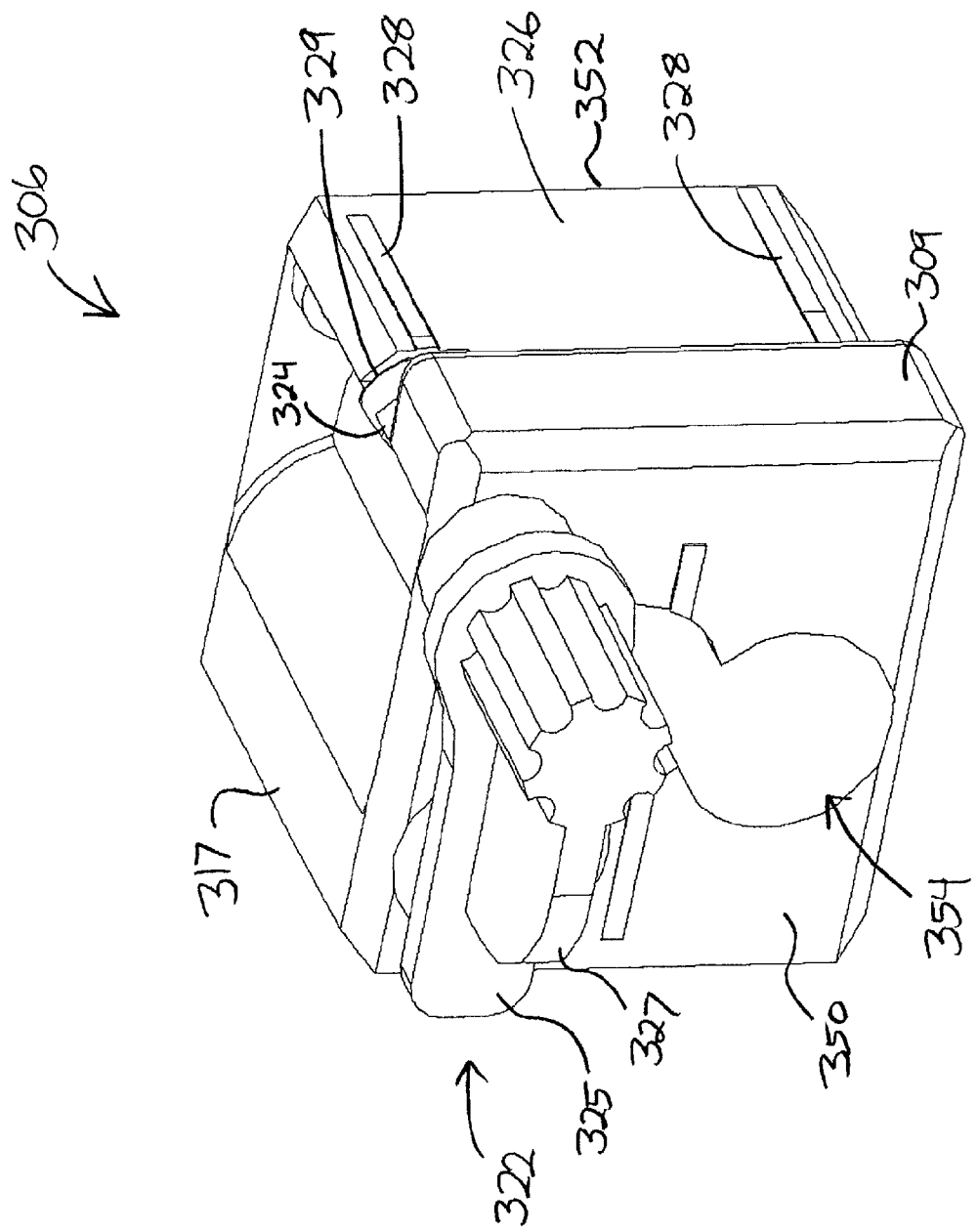
FIG. 19C is a front perspective view of the guide cube of FIG. 19A, with the lock in a locked position.
Figure 19D:
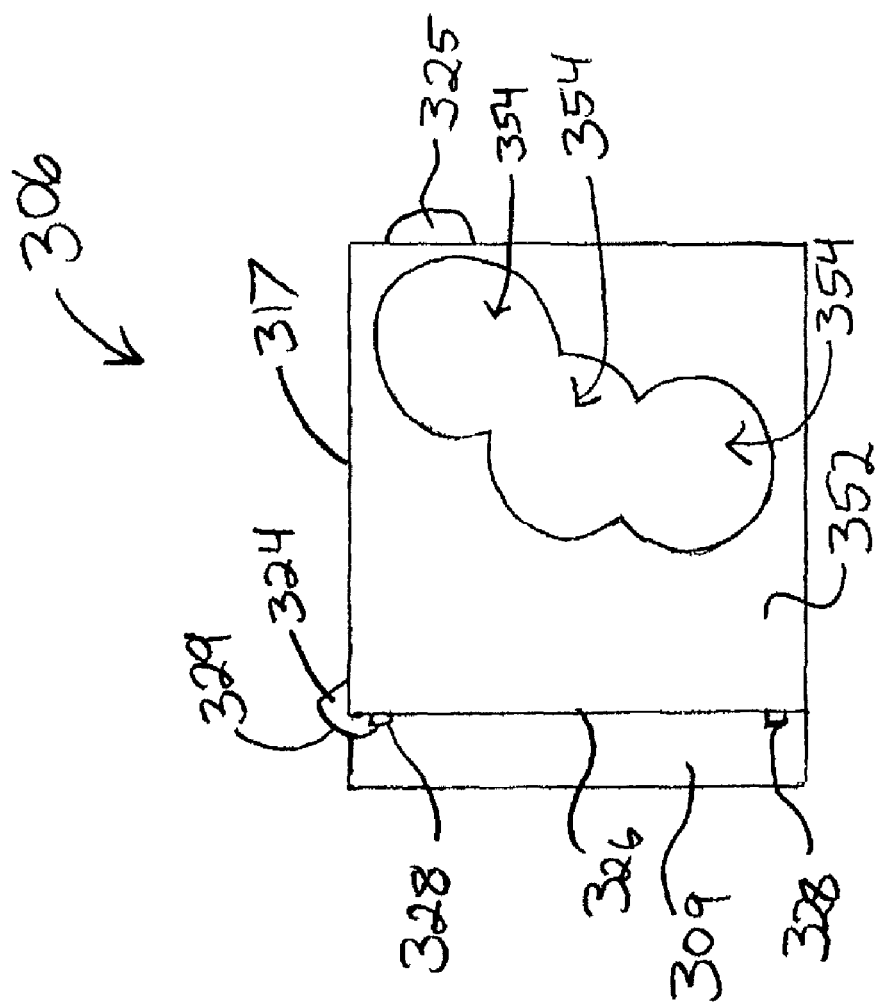
FIG. 19D is a rear elevational view of the guide cube of FIG. 19C, with the lock in the locked position.
Figure 20:
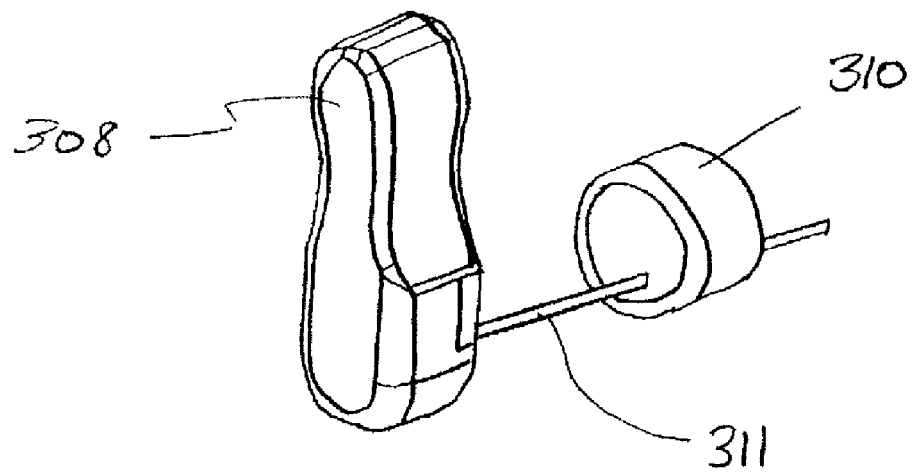
FIG. 20 is a front perspective view of the eccentric lock of FIG. 16 without the guide cube shown.

FIGS. 19A-19B show connection member (324) in an unlocked position, whereby connection member (324) does not extend outwardly past the planes defined by sides (317, 326) of guide cube (306). FIGS. 19C-19D show connection member (324) in a locked position after lever (322) has been rotated, whereby cutting edge (329) extends outwardly past the planes defined by sides (317, 326) of guide cube (306). The extension of cutting edge (329) shown in FIGS. 19C-19D allows cutting edge (329) to "dig into" one or more inner portions of a selected square recess (130) of grid plate (96), thereby substantially locking guide cube (306) into a secure position. Connection member (324) may thus move into engagement with the sidewall interior of grid plate (96), similar to locking member (320) as described above. Also like locking member (320) described above, connection member (324) of this example may be subsequently disengaged from the inner sidewall of square recess (130) by rotating lever (322) in the opposite direction to permit removal of guide cube (306) from grid plate (96). Of course, connection member (324) may have any other suitable configurations, properties, operability, etc.

Guide cube (306) of the present example further comprises fins (328), which may be provided in pairs on opposing sides of the body of guide cube (306). Fins (328) of the present example extend outwardly, and are tapered along their length. In particular, fins (328) extend outwardly to a greater degree near front face (350) of guide cube (306) than they do near rear face (352) of guide cube (306). In other words, fins (328) taper progressively outward as they approach front face (350), to progressively reduce clearance between guide cube (306) and the inner sidewall of square recess (130) in grid plate (96). Fins (328) may be substantially rigid, elastomeric, or have any other suitable properties. Of course, fins (328) may be provided on any other guide cube (300, 302, 304) described herein; or fins (328) may simply be omitted altogether.

Figure 19E:
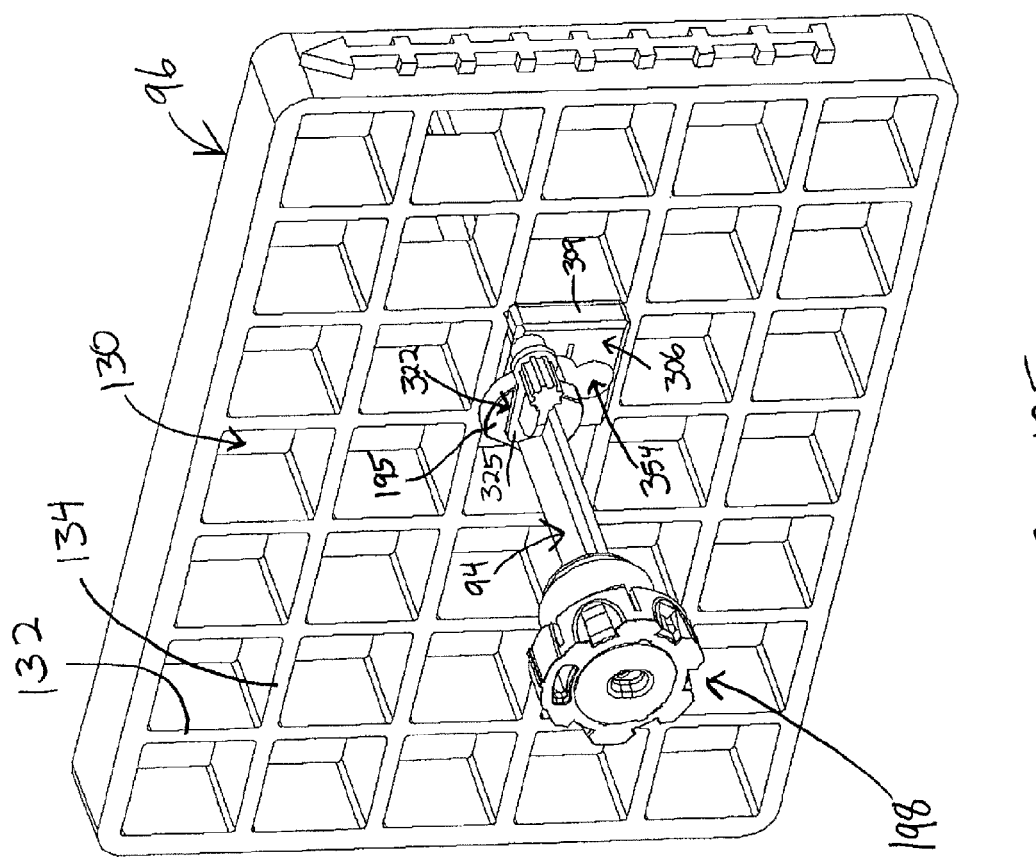
FIG. 19E is a front perspective view of the guide cube of FIG. 19A inserted in an exemplary grid plate, coupled with an exemplary cannula assembly.

In some versions, lever (322) may comprise a first lever section (325) and a second lever section (327). In some such versions, first lever section (325) may engage depth stop device (195) (e.g., with depth stop device (195) being similar to depth stop device (95) shown in FIG. 7 and described above) to restrict longitudinal movement of cannula (94) when cannula (94) is inserted in guide cube (306) and lever (322) is sufficiently rotated. In particular, the distal face of first lever section (325) may be spaced away from front face (350) of guide cube (306) to a distance approximating the thickness of depth stop device (195). An example of first lever section (325) engaging a depth stop device (195) is shown in FIG. 19E and is described in greater detail below.

In an exemplary use, guide cube (306) may first be inserted into a selected square recess (130) of grid plate (96). Cannula (94), with a depth stop device (195) fitted thereon, may then be inserted into a selected guide passageway (354) of guide cube (306) until depth stop device (195) engages front face (350) of guide cube (306). At this point, engagement between depth stop device (195) and front face (350) of guide cube (306) may prevent cannula (94) from longitudinally moving any further distally (or at least provide some degree of resistance to further distal longitudinal movement of cannula (94) in guide cube (306)). Then, the user may rotate lever (322) until lever (322) contacts cannula (94). At this point, connection member (324) may dig into the inner sidewall of square recess (130) in guide plate (96) to anchor guide cube (306) in guide plate (96). In addition, at this point, first lever section (325) may essentially constrain or "trap" depth stop device (195) between the distal face of first lever section (325) and front face (350) of guide cube (306), thereby substantially preventing cannula (94) from longitudinally moving any further proximally until lever (322) is rotated away from cannula (94). An example of such "trapping" of depth stop device (195) is shown in FIG. 19E. In some versions, cannula (94) may still be rotated about its longitudinal axis despite depth stop device (195) being "trapped" between first lever section (325) and front face (350) of guide cube (306).

Of course, lever (322) may lack such a first lever section (325); and lever (322) need not necessarily "trap" depth stop device (195). Indeed, lever (322) may have any other suitable configuration. It should also be understood that lever (308) may alternatively be configured in accordance with lever (322), including but not limited to having a similar first lever section (325) that "traps" a depth stop device (195) between lever (308) and the guide cube (300, 302).

While knobs (312) and levers (308, 322) have been described above as providing rotation of a locking component in cubes (300, 302, 304, 306), it should be understood that a variety of other structures, features, or components may be used to provide rotation of a locking component. Furthermore, cubes (300, 302, 304, 306) may alternatively be configured such that a non-rotating structure, feature, or component is used to provide either rotational or non-rotational movement of a locking component. By way of example only, cube (300, 302, 304, 306) may include a button or a slider that is operable to selectively engage and/or disengage a locking component of cube (300, 302, 304, 306) relative to a sidewall or other portion of grid plate (96). Suitable variations for providing such selective engagement and disengagement will be apparent to those of ordinary skill in the art in view of the teachings herein. Can also use any other type of structure in addition to or in lieu of knobs/levers.

D. Elastomeric Inserts

While some features of guide cubes (300, 302, 304, 306) may assist in securing guide cube (300, 302, 304, 306) within a grid plate (96), other features may assist in securing an instrument such as a biopsy device (14) or a portion of a biopsy device (14) (e.g., needle (90) of biopsy device (14), a combination of cannula (94) and obturator (92), etc.) within guide cube (300, 302, 304, 306). In FIGS. 16 and 17, elastomeric inserts (330) fit within guide holes (332, 334). Elastomeric inserts (330) are designed such that the opening in the inserts (330) is smaller in diameter than the diameter of the instrument, e.g. cannula (94). When cannula (94) is inserted in guide hole (332, 334), insert (330) compresses to provide for a secure fit. In other words, while insert (330) permits insertion of cannula (94) or needle (90), etc., through a selected guide hole (332, 334), friction between the inserted instrument and the elastomeric material of insert (330) provides some resistance to axial movement of the inserted instrument relative to guide hole (332, 334). In some versions, the securing force provided by insert (330) is such that the compressed tissue of a patient will not displace cannula (94) proximally from guide hole (332, 334) during a biopsy procedure.

Based on the teachings herein, those of ordinary skill in the art will appreciate that inserts (330) may be removable and available in different sizes and with different compressive characteristics and/or frictional characteristics. Thus, in some versions, use of removable inserts (330) permits guide cubes (300, 302, 304) to be used with instruments of various diameters, such as various sized biopsy devices or various sized portions of biopsy devices, such as needles, cannulas, obturators, or combinations of these and other components.

In some versions inserts (330) may be integrally molded with guide cube (300, 302, 304). In some such versions, inserts (330) may extend partially into guide holes or inserts (330) may extend fully through guide holes. In some other versions, inserts (330) and guide cube (300, 302, 304) are molded separately, and insert (330) is then secured to guide cube (300, 302, 304) in any suitable fashion (e.g., using adhesive, etc.). Various suitable ways in which inserts (330) and guide cube (300) may be molded together or otherwise secured together will be apparent to those of ordinary skill in the art in view of the teachings herein.

Inserts (330) may be constructed from any suitable compressive material. Based on the teachings herein, those of ordinary skill in the art will appreciate that several elastomeric materials may be suitable for use with inserts (330). By way of example only, suitable elastomeric materials may include thermosetting plastics that may require vulcanization, thermoplastic elastomers (e.g. Santoprene™ among others), natural rubber, synthetic rubbers (e.g. ethylene propylene diene M-class—EPDM—among others), and other polymers having suitable elastic properties.

E. Retaining Rings

Referring to FIGS. 18A-18D, guide cube (304) includes guide holes (336, 338). Guide holes (336, 338) include retaining rings (340) that may be positioned around a portion of a biopsy instrument, e.g., cannula (94). Retaining rings (340) may be constructed from a compressible elastomeric material. Retaining rings (340) are designed such that the opening defined by retaining ring (340) is smaller in diameter than the diameter of the instrument, e.g., cannula (94). For instance, retaining ring (340) may define a relatively small inner diameter that is radially consistent throughout the circumference of the opening defined by retaining ring (340). Alternatively, retaining ring (340) may include several protrusions that project radially inward, with such protrusions collectively defining the relatively small inner diameter. When cannula (94) is inserted in guide hole (336, 338), retaining ring (340) compresses to provide for a secure fit. In other words, while retaining ring (340) permits insertion of cannula (94) or needle (90), etc., through a selected guide hole (336, 338), friction between the inserted instrument and the elastomeric material of retaining ring (340) provides some resistance to axial movement of the inserted instrument relative to guide hole (336, 338). In some versions, the securing force provided by retaining ring (340) is such that the compressed tissue of a patient will not displace cannula (94) proximally from guide hole (336, 338) during a biopsy procedure.

In some versions, retaining ring (340) is formed by a sheet that is molded within or otherwise provided within guide cube (304). Such a sheet may extend to reach both guide holes (336, 338). Thus, retaining ring (340) need not be truly ring-shaped. In some other versions, each retaining ring (340) is formed separately. In still other versions, an annular groove is formed within the passageway of guide hole (336, 338), and an elastomeric member (e.g., o-ring, etc.) is positioned within the annular groove. For instance, such an elastomeric member may have an uncompressed outer diameter that is greater than the inner diameter defined by the passageway of guide hole (336, 338), and perhaps even greater than the inner diameter defined by the annular groove that is within the passageway of guide hole (336, 338). In some such versions, the elastomeric member may be positioned about cannula (94) before cannula (94) is inserted in guide hole (336, 338). As cannula (94) is inserted in guide hole (336, 338), the elastomeric member may compress to fit within guide hole (336, 338). When the elastomeric member reaches the annular groove, the elastomeric member may expand and fit within the annular groove.

It should also be understood that each guide hole (336, 338) may have more than one associated retaining ring (340). For instance, each guide hole (336, 338) may have two or more retaining rings (340) that are axially staggered along the length of guide hole (336, 338). Furthermore, a cube (300, 302, 304, 306) may have inserts (332, 332) in addition to having retaining rings (340), among other various components.

In the present example, each guide cube (300, 302, 304, 306) includes a grounding feature (309) on the side of its proximal face (315). Grounding feature (309) is configured to restrict the extent to which guide cube (300, 302, 304, 306) may be inserted in grid plate (96). In particular, depending on the rotational position of guide cube (300, 302, 304, 306) as it is inserted in grid plate (96), grounding feature (309) is configured to engage vertical bar (132) or horizontal bar (134) of grid plate (96) to prevent further insertion of guide cube (300, 302, 304, 306). While grounding feature (309) is shown as being located at one corner edge of proximal face (315), it should be understood that a grounding feature (309) may be located at two or more corner edges of proximal face (315). It should also be understood that a variety of alternative structures, features, or components may be incorporated into guide cube (300, 302, 304, 306) and/or grid plate (96) to restrict the extent to which guide cube (300, 302, 304, 306) may be inserted in grid plate (96).

As noted above, any guide cube (104, 104a, 104b, 104c, 300, 302, 304, 306) described herein may be used in a procedure that includes the use of PEM imaging, BSGI imaging, or any other suitable type of imaging. By way of example only, a guide cube (104, 104a, 104b, 104c, 300, 302, 304, 306) may be used with a grid plate (96) that is configured for use in an MRI setting, a grid plate for use in a nuclear/molecular imaging setting, or with some other type of cube holder (e.g., "guide holder") used in nuclear/molecular imaging or other type of imaging. For instance, a suitable alternative cube holder or "guide holder" may include fewer openings (e.g., one to four) that are configured to receive a guide cube (104, 104a, 104b, 104c, 300, 302, 304, 306) as compared to the number of recesses (130) in grid plate (96). Furthermore, a guide cube (104, 104a, 104b, 104c, 300, 302, 304, 306) may be used with a biopsy device (14) in conjunction with a full targeting set or with just a biopsy device (14) (e.g., in settings where a radioisotope can be communicated through the biopsy device (14)). It should also be understood that a guide cube (104, 104a, 104b, 104c, 300, 302, 304, 306) may be used just with a radioisotope, without necessarily involving any biopsy device (14). For instance, a radioisotope may be provided on or through an implement that has a sharp tip, and the implement may be inserted through the guide cube (104, 104a, 104b, 104c, 300, 302, 304, 306). Still other various settings and combinations in which a guide cube (104, 104a, 104b, 104c, 300, 302, 304, 306) may be used will be apparent to those of ordinary skill in the art in view of the teachings herein.

While several guide cubes have been discussed in detail above, it should be understood that the components, features, configurations, and methods of using the guide cubes discussed are not limited to the contexts provided above. In particular, components, features, configurations, and methods of use described in the context of one of the guide cubes may be incorporated into any of the other guide cubes. One merely exemplary additional feature that may be provided in any of the guide cubes described herein is one or more ridges on one or more external faces of the cube. Such ridges may be substantially rigid, elastomeric, or have any other suitable properties. Such ridges may provide a more secure fit between a cube and grid (e.g., reducing the likelihood that that the guide cube will undesirably fall out of the grid plate), may permit a single cube to be inserted in different grids having differently sized openings, and/or may provide other results. Still other additional and alternative suitable components, features, configurations, and methods of using the guide cubes will be apparent to those of ordinary skill in the art in view of the teachings herein.

Versions of the present invention have application in conventional endoscopic and open surgical instrumentation as well as application in robotic-assisted surgery.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various versions in the present disclosure, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

What is claimed is:

1. A guide device for guiding a medical instrument relative to a patient, the guide device being usable with a first plate and a second plate, wherein the first plate has a frame defining a plurality of apertures, wherein the second plate and the first plate are adjustable to secure a portion of the patient, wherein the guide device is configured to be coupled with a selected one of the apertures of the first plate, the guide device comprising:
   a. a body defined by at least one surface, wherein the at least one surface comprises a generally proximal portion of the body and a generally distal portion of the body;
   b. at least one passageway, wherein the at least one passageway extends from the generally proximal portion through the body and to the generally distal portion, wherein the at least one passageway is configured to receive at least a portion of the medical instrument; and
   c. a lock operatively configured to engage the first plate, wherein the lock is further operatively configured to selectively and removably secure the guide device within the selected one of the apertures of the first plate.

2. The guide device of claim 1, wherein the lock comprises an actuating member and a locking member, wherein the actuating member is operatively configured to move the locking member from an unlocked position to a locked position, wherein in the locked position the locking member engages the first plate.

3. The guide device of claim 2, wherein the locking member and the actuating member are connected by a shaft, wherein the actuating member is operatively configured to rotate the shaft about an axis of rotation, wherein the shaft is operatively configured to rotate the locking member.

4. The guide device of claim 3, wherein the locking member is configured to rotate eccentrically about the axis of rotation.

5. The guide device of claim 2, wherein the actuating member comprises a selected one of a knob or a lever.

6. The guide device of claim 2, wherein the locking member comprises a wheel, wherein in the locked position the wheel contacts at least one inner surface of the selected one of the apertures of the first plate.

7. The guide device of claim 6, wherein the wheel comprises an elastomeric portion, wherein the elastomeric portion is operatively configured to compress in response to the wheel contacting the at least one inner surface of the selected one of the apertures of the first plate.

8. The guide device of claim 7, wherein the elastomeric portion is comprised of a material selected from the group consisting of vulcanized thermosetting plastics, thermoplastic elastomers, natural rubber, synthetic rubber, and combinations thereof.

9. The guide device of claim 6, wherein the wheel further comprises a curved surface portion and a flat surface portion.

10. The guide device of claim 6, wherein the guide device further comprises a grounding structure operatively configured to prevent over-insertion of the guide device.

11. The guide device of claim 2, wherein the locking member comprises a rigid structure, wherein in the locked position the locking member contacts at least one inner surface of the selected one of the apertures of the first plate.

12. The guide device of claim 11, wherein the locking member is harder than the at least one inner surface of the selected one of the apertures of the first plate.

13. The guide device of claim 12, wherein the locking member is configured to dig into the at least one inner surface of the selected one of the apertures of the first plate when the locking member is moved to the locked position.

14. The guide device of claim 2, wherein the locking member comprises a rigid structure, wherein in the locked position the locking member contacts the frame of the first plate.

15. The guide device of claim 14, wherein the locking member comprises a ceramic structure having a conical shape.

16. The guide device of claim 2, further comprising a brake, wherein the brake is operatively configured to stop rotation of the actuating member.

17. A guide device insertable into a grid plate for guiding a medical instrument relative to a patient, the guide device comprising:
   a. a body defined by a plurality of faces, wherein the plurality of faces comprise at least one proximal face and at least one distal face, wherein the body is configured to be selectively and removably locked in the grid plate;
   b. at least one passageway, wherein the at least one passageway extends from the proximal face through the body to the distal face, wherein the at least one passageway is configured to receive at least a portion of the medical instrument; and
   c. a restricting member, wherein the restricting member is positioned within the at least one passageway, wherein the restricting member is operatively configured to restrict the medical instrument from proximal displacement after the medical instrument has been inserted in the passageway.

18. The guide device of claim 17, wherein the restricting member comprises an elastomeric insert.

19. The guide device of claim 17, wherein the restricting member comprises a groove, wherein the groove is operatively configured to receive an o-ring.

20. The guide device of claim 17, wherein the restricting member includes a plurality of protrusions projecting radially inward.

* * * * *